United States Patent [19]

Yoneda et al.

[11] Patent Number: 4,508,727

[45] Date of Patent: Apr. 2, 1985

[54] ANTIHYPERTENSIVE 2-OXO-IMIDAZOLIDINE DERIVATIVES

[75] Inventors: Naoto Yoneda, Suita; Jyoji Kato, Yawata; Kimiaki Hayashi, Suita; Takashi Ochiai, Kobe; Keizo Kinashi, Yao, all of Japan

[73] Assignee: Tanabe Seiyaku Co., Ltd., Osaka, Japan

[21] Appl. No.: 496,877

[22] Filed: May 24, 1983

[30] Foreign Application Priority Data

May 24, 1982 [JP] Japan .................. 57-88637

[51] Int. Cl.³ .................. A61K 31/415; C07D 233/38
[52] U.S. Cl. .................. 514/398; 548/321
[58] Field of Search .................. 548/321; 424/273 R

[56] References Cited

U.S. PATENT DOCUMENTS 4,374,829 2/1983 Harris et al. .................. 424/177
4,380,644 4/1983 Yoneda et al. .................. 548/321

FOREIGN PATENT DOCUMENTS 0012401 6/1980 European Pat. Off. .
48159 3/1982 European Pat. Off. .
0050866 5/1982 European Pat. Off. .......... 548/534
35114 3/1983 Japan .

OTHER PUBLICATIONS

Goulden, C. H., *Methods of Statistical Analysis*, John Wiley & Sons, Inc., New York, 1939, pp. 52–64.

*Primary Examiner*—Richard A. Schwartz
*Attorney, Agent, or Firm*—Browdy and Neimark

[57] ABSTRACT

Novel 2-oxo-imidazolidine derivative of the formula:

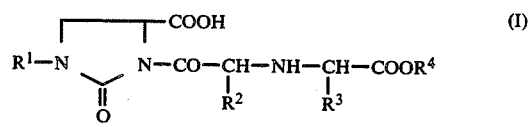

wherein $R^1$ is lower alkyl or phenyl-lower alkyl, $R^2$ is lower alkyl, $R^3$ is alkyl of one to 12 carbon atoms or phenyl-lower alkyl and $R^4$ is hydrogen or lower alkyl, and a pharmaceutically acceptable salts thereof are disclsoed. Said compounds (I) and salts thereof are useful as hypotensive agents.

9 Claims, No Drawings

ANTIHYPERTENSIVE 2-OXO-IMIDAZOLIDINE DERIVATIVES

This invention relates to a novel 2-oxo-imidazolidine derivative and a process for preparing same. More particularly, it relates to a compound of the formula:

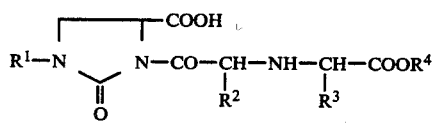

wherein $R^1$ is lower alkyl or phenyl-lower alkyl, $R^2$ is lower alkyl, $R^3$ is alkyl of one to 12 carbon atoms or phenyl-lower alkyl and $R^4$ is hydrogen or lower alkyl, or a pharmaceutically acceptable salt thereof.

It is known that the enzyme renin splits a leucyl-leucine bond of angiotensinogen to produce angiotensin I. Angiotensin I is converted by angiotensin-converting enzyme (ACE) to angiotensin II which is an active pressor substance and causative of various forms of hypertension in mammalian species. It is also known that ACE decomposes and inactivates bradykinin, thereby serving to increase blood pressure. Thus, intensive studies have been made in recent years to investigate ACE-inhibitors because such inhibitors may be used for the treatment of patient with high blood pressure.

As a result of various investigations, we have now found that the novel 2-oxo-imidazolidine derivative (I) of the present invention shows potent inhibitory activity against ACE and is useful to reduce or relieve angiotensin-related hypertension. For example, when the ACE-inhibitory activity was estimated in vivo by the use of rats which were administered angiotensin I intravenously, (4S)-1-methyl-3-[(2S)-2-[N-((1S)-1-ethoxycarbonyl-3-phenylpropyl)amino]propionyl]-2-oxo-imidazolidine-4-carboxylic acid at a dose of 1.0 mg/kg showed about 60% inhibition of ACE-activity. Moreover, when a test compound was administered orally to spontaneously hypertensive rats, (4S)-1-methyl-3-{(2S)-2-[N-((1S)-1-ethoxycarbonyl-3-phenylpropyl)amino]-propionyl}-2-oxo-imidazolidine-4-carboxylic acid at a dose of 3 mg/kg showed a decrease of about 45 mmHg in blood pressure and said hypotensive activity of the test compound lasted for more than 6 hours. Further, the toxicity of the compound (I) of the invention is remarkably low. For example, when (4S)-1-benzyl-3-{(2S)-2-[N-((1S)-1-carboxy-3-phenylpropyl)amino]propionyl}-2-oxo-imidazolidine-4-carboxylic acid and (4S)-1-methyl-3-{(2S)-2-[N-((1S)-1-carboxy-n-nonyl)amino]-propionyl}-2-oxo-imidazolidine-4-carboxylic acid were administered intravenously to mice at the dose of 1000 mg/kg, no mice died 7 days after the administration. Thus, angiotensin-dependent hypertension in mammals can be alleviated by administration of the compound (I) of the present invention or a pharmaceutically acceptable salt thereof.

In the compound (I) of the present invention, representative examples of $R^1$ include lower alkyl of one to four carbon atoms such as methyl, ethyl, n-propyl, isopropyl, n-butyl or isobutyl; and phenyl-lower alkyl such as benzyl, phenethyl, phenylpropyl or phenylbutyl. On the other hand, representative examples of $R^2$ include lower alkyl of one to four carbon atoms such as methyl, ethyl, n-propyl, isopropyl, n-butyl or isobutyl. Representative examples of $R^3$ include alkyl of one to 12 carbon atoms such as methyl, ethyl, n-propyl, isopropyl, n-butyl, isobutyl, n-pentyl, isopentyl, n-hexyl, isohexyl, n-heptyl, isoheptyl, n-octyl, isooctyl, n-nonyl, isononyl, n-decyl, isodecyl, n-undecyl, isoundecyl, n-dodecyl or isododecyl; and phenyl-lower alkyl such as benzyl, phenethyl, phenylpropyl or phenylbutyl. Representative examples of $R^4$ include hydrogen; lower alkyl of one to four carbon atoms such as methyl, ethyl, n-propyl, isopropyl, n-butyl or isobutyl. Among the compounds of the present invention, a preferred subgenus is those of the formula (I) in which $R^1$ is alkyl of one to four carbon atoms or benzyl, $R^2$ is alkyl of one to four carbon atoms, $R^3$ is straight or branched alkyl of 4 to 8 carbon atoms, benzyl or phenethyl and $R^4$ is hydrogen or alkyl of one to four carbon atoms. Another preferred subgenus is the compound of the formula (I) in which $R^1$ is methyl, n-butyl or benzyl, $R^2$ is methyl or ethyl, $R^3$ is isobutyl, isopentyl, n-octyl, benzyl or phenethyl and $R^4$ is hydrogen, ethyl or n-butyl. Other preferred subgenus is the compound of the formula (I) in which $R^1$ is methyl, $R^2$ is methyl, $R^3$ is n-octyl or phenethyl and $R^4$ is hydrogen or ethyl.

While the compound (I) of the present invention can exist in the form of four diastereoisomers or eight optical isomers due to the three asymmetric carbon atoms involved therein, all of these optical isomers or a mixture thereof are included within the scope of the invention. Among said optical isomer, however, the compound (I) in which the carbon atoms at the 4th-position of oxoimidazolidine ring and at the 2nd-position of the amino acid moiety of the formula: —NH—CH($R^3$—)COOR$^4$ have S-configuration is preferred for medicinal use. The compound (I) of the invention in which the carbon atoms at the 4th-position of oxoimidazolidine ring, at the 2nd-position of the alkanoyl moiety of the formula: —COCH($R^2$)— and at the 2nd-position of the amino acid moiety of the formula: —NH—CH($R^3$—)COOR$^4$ have S-configuration is most preferred for medicinal use.

The compound (I) of the invention can be used for pharmaceutical use either as the free acid (and/or base) or a salt thereof, and can form salts with either organic and inorganic acids or organic and inorganic bases. Pharmaceutically acceptable acid addition salts of the compound (I) include, for example, organic acid addition salts such as succinate, maleate, fumalate and methanesulfonate and inorganic acid addition salts such as hydrochloride, hydrobromide, sulfate and phosphate. On the other hand, pharmaceutically acceptable salts of the compound (I) with organic or inorganic bases include, for example, sodium, potassium, calcium and magnesium salts; or lysine, ornithine and dicyclohexylamine salts.

A daily dose of the compound (I) of the present invention will vary depending on severity of disease, age, weight or conditions of patients and other factors. A suitable daily dose of the compound (I) or a salt thereof may be about 1 to about 1000 mg, especially 10 to 500 mg, per body of patients.

Further, the compound (I) or a salt thereof may be used in the form of a pharmaceutical preparation containing the same compound in conjunction or admixture with a pharmaceutical excipient suitable for oral or parenteral administration. Suitable excipients include, for example, starch, lactose, glucose, potassium phosphate, corn starch, arabic gum, stearic acid and other known medicinal excipients. The pharmaceutical preparations may be in solid form such as tablets, pills, capsules or suppositories; or in liquid form such as solutions, suspensions or emulsions. They may be sterilized and/or may further contain auxiliaries such as stabilizing, wetting or emulsifying agent.

According to the present invention, the compound (I) can be prepared by subjecting the compound of the formulae:

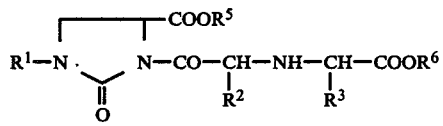
(II)

wherein $R^5$ is a protecting group capable of being removed by acid treatment or catalytic hydrogenation, $R^6$ is lower alkyl or a protecting group capable of being removed by acid treatment or catalytic hydrogenation and $R^1$, $R^2$ and $R^3$ are the same as defined above, to acid treatment and/or catalytic hydrogenation.

In the above-mentioned compound (II), representative examples of the protecting group ($R^5$ and/or $R^6$) include tert.-butyl and benzyl. If tert.-butyl is used as the protecting group, the removal of said protecting group ($R^5$ and/or $R^6$) can be easily accomplished. For example, said removal of the protecting group is preferably carried out by contacting the compound (II) with an acid in an inert solvent. Suitable examples of the acid include hydrogen chloride, hydrogen bromide, hydrogen fluoride, trifluoroacetic acid and the like. Dioxane, tetrahydrofuran and ethyl acetate are suitable as the inert solvent. It is preferred to carry out the reaction at a temperature between 0° C. and 50° C., especially at a temperature of 20° C. to 30° C. On the other hand, if benzyl is used as the protecting group ($R^5$ and/or $R^6$), the removal of said protecting group can be effected by catalytic hydrogenation. This catalytic hydrogenation is carried out in the presence of a catalyst in a hydrogen gas atmosphere in a solvent. Preferred examples of the catalyst include palladium black, palladium-carbon, platinum oxide and the like. Lower alkanols such as methanol, ethanol and propanol are suitable as the solvent. It is preferred to carry out the reaction at a temperature of about 20° C. to 40° C. under one to 5 atmospheric pressure and under shaking. For example, said reaction proceeds smoothly at about 25° C. under atmospheric pressure.

In the above-mentioned reactions, the compound (II) may be used in the form of either optically active isomer or a mixture thereof. Since said reactions proceed without racemization, the compound (I) is readily obtained either in the form of optically active isomer or a mixture thereof by the use of the corresponding optically active isomer of the compound (II) or a mixture thereof.

The compound (I) of the present invention may be readily converted into a pharmaceutically acceptable salt thereof in conventional manner, for example, by neutralization with a base or an acid.

The compound (II) which is used in the process of the present invention is also novel and can be prepared according to the methods shown by the following reaction scheme:

[Method A]

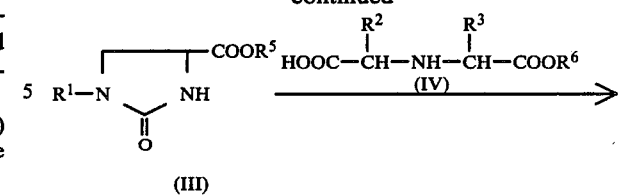
(III)    (IV)

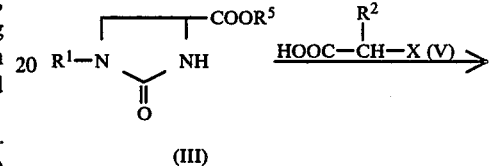
(II)

[Method B]

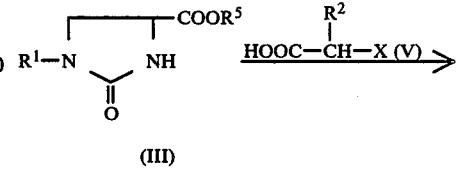
(III)

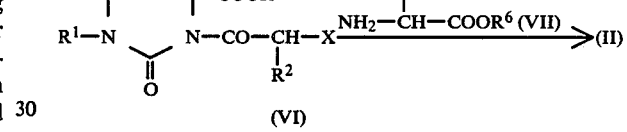
(VI)

wherein X is halogen, alkyl sulfonyloxy or aryl sulfonyloxy and $R^1$, $R^2$, $R^3$, $R^5$ and $R^6$ are the same as defined above.

In the above-mentioned reaction scheme, the compound (III) can be prepared, for example, by condensing 3-benzyloxycarbonyl-2-oxo-imidazolidine-4-carboxylic acid (cf. Justus Liebich's. Annalen der Chemie., 529, 1 (1937)) with an alcohol of the formula: $R^5$—OH (wherein $R^5$ is the same as defined above) to give 3-benzyloxycarbonyl-2-oxo-imidazolidine-4-carboxylate, reacting said ester with a halogeno compound of the formula: $R^1$—X' (wherein X' is halogen and $R^1$ is the same as defined above) to give 1-substituted-3-benzyloxycarbonyl-2-oxo-imidazolidine-4-carboxylate, and then subjecting the product to catalytic hydrogenation. The starting compound, i.e., 3-benzyloxycarbonyl-2-oxo-imidazolidine-4-carboxylic acid, may be used in the form of either racemic modification or optically active isomer thereof. Moreover, the compound (III) in an optically active form may be readily obtained by the use of the corresponding optically active isomer of 3-benzyloxycarbonyl-2-oxo-imidazolidine-4-carboxylic acid because all these reactions proceed without racemization.

According to Method A, the compound (II) is prepared by condensing the compound (III) with a reactive derivative of the compound (IV). The condensation reaction of the compound (III) with the reactive derivative of the compound (IV) can be conducted in the presence of a base in a solvent. Suitable examples of the reactive derivative of the compound (IV) include the corresponding active esters (e.g., succinimide ester, benzotriazole ester). Tetrahydrofuran, dioxane, and methylene chloride are suitable as the solvent. Moreover, suitable examples of the base include alkali metal alkoxides (e.g., potassium tert.-butoxide, sodium ethoxide) and alkali metal hydrides (e.g., sodium hydride). It is preferred to carry out the reaction at a temperature between $-60°$ C. and $20°$ C., especially at a temperature of $-40°$ C. to $0°$ C.

In this reaction, the compound (III) and the reactive derivative of the compound (IV) may be used in the form of either optically active isomer or a mixture thereof. The optically active isomer of the compound (II) is obtained from the corresponding optically active isomer of the compounds (III) and (IV) without racemization. Moreover, the compound (IV) may be prepared by reacting an amino acid ester of the formula: $NH_2$—$CH(R^2)$—$COOR^7$ (VIII) (wherein $R^7$ is tert.-butyl or benzyl and $R^2$ is the same as defined above) with a compound of the formula: X—CH(R$^3$)—COOR$^6$ (IX) (wherein X is halogen, alkyl sulfonyloxy or aryl sulfonyloxy and $R^3$ and $R^6$ are the same as defined above), or reacting a halogeno-alkanoic acid ester of the formula: $R^7OOC$—$CH(R^2)$—X (X) (wherein $R^2$, $R^7$ and X are the same as defined above) with a compound of the formula: $NH_2$—$CH(R^3)$—$COOR^6$ (VII) (wherein $R^3$ and $R^6$ are the same as defined above) in a manner known per se, and then removing the protecting group ($R^7$) from the resultant compound of the formula: $R^7OOC$—$CH(R^2)$—$NH$—$CH(R^3)$—$COOR^6$ (XI). If the compound (XI) obtained in this reaction is a mixture of two isomers, said isomers may be separated into each isomers thereof by silica gel chromatography and/or fractional crystallization. The fractional crystallization is carried out by forming the salt of the compound (XI) with maleic acid, and recovering the less soluble isomer from the reaction mixture. In this fractional crystallization procedure, the compound (XI) having S-configuration at both of the 2nd-position of the alkanoic moiety and the 2nd-position of the amino acid moiety forms the less soluble diastereomeric salt. The removal of the protecting group from the compound (XI) can be reasily conducted by subjecting the compound (XI) to acid treatment or catalytic hydrogenation.

On the other hand, according to Method B, the compound (II) is prepared by condensing the compound (III) with the reactive derivative of the compound (V) to give the compound (VI), and condensing said compound (VI) with the compound (VII). The condensation reaction of the compound (III) with the reactive derivative of the compound (V) can be conducted in the presence of an acid acceptor in a solvent. Suitable examples of the reactive derivative of the compound (V) include the corresponding acid halide (e.g., acid chloride, acid bromide). Moreover, suitable examples of the group X in the compound (V) include halogen such as chlorine, bromine or iodine; alkyl sulfonyloxy such as methanesulfonyloxy or ethanesulfonyloxy; and aryl sulfonyloxy such as p-toluenesulfonyloxy. Suitable examples of the acid acceptor include alkali metal alkoxides (e.g., potassium tert.-butoxide, sodium ethoxide) and alkali metal hydrides (e.g., sodium hydride). Tetrahydrofuran, dioxane, methylene chloride, chloroform and acetonitril are suitable as the solvent. It is preferred to carry out the reaction at a temperature between $-60°$ C. and $20°$ C., especially at a temperature of $-40°$ C. to $0°$ C.

The second step, i.e., the condensation reaction of the compound (VI) with the compound (VII), can be conducted in the presence of an acid acceptor in a solvent. Suitable examples of the acid acceptor include alkali metal carbonate such as potassium carbonate, sodium carbonate; alkali metal hydrogen carbonate such as sodium bicarbonate; organic tertiary amine such as 1,8-diazabicyclo[5.4.0]undecene-7. Hexamethylphosphoric triamide, dimethylformamide and tetrahydrofuran are suitable as the solvent. It is preferred to carry out the reaction at a temperature between $0°$ C. and $80°$ C., especially at a temperature of $20°$ C. to $50°$ C.

In the above-mentioned reactions, the compounds (III), (V) and (VII) may be used in the form of either racemic modification or optically active isomer thereof. When the compound (II) obtained in these reactions is a mixture of isomers, said compound (II) may be separated into each isomers thereof by silica gel column chromatography. Concomitantly, the amino acid of the formula (VII) in which $R^3$ is phenethyl and n-octyl are obtained according to the method described in J. Med. Chem., 11, 1258, (1968) and J. Org. Chem., 41, 3491, (1976), and an optically active isomer of said amino acid may be obtained by enzymic resolution of the racemic modification thereof with an aminoacylase.

Practical and presently-preferred embodiments of the present invention are illustratively shown in the following Examples. Throughout the specification and claims, the term "lower alkyl" should be interpreted as referring to alkyl of one to four carbon atoms and the term "alkyl" should be interpreted as referring to alkyl of one to 12 carbon atoms.

EXPERIMENT 1

ACE-inhibitory activity in vitro

50 μl of a solution containing 0.01 mole/liter of hippuryl-histidyl-leucine (substrate) and 0–100 μl of a test compound solution were added to 300 μl of a 0.2M tris-hydrochloric acid buffer solution containing 0.2 mole/liter of sodium chloride. The total volume of said mixture was adjusted to 450 μl with water. Then, 50 μl of angiotensin-converting enzyme (ACE) isolated from pig's renal cortex were added to the mixture, and the mixture was allowed to stand at $37°$ C. for 20 minutes. The amount of histidyl-leucine produced from the substrate by the action of ACE was assayed microbiologically by the use of Leuconostoc mesenteroides P-60, and the ACE-inhibitory activity of the test compound was estimated therefrom. The results are shown in the following Table 1.

TABLE 1

$$R^1-N\underset{\underset{O}{\|}}{\overset{\overset{(S)}{\overset{|}{\text{COOH}}}}{\diagup\diagdown}}N-CO-\underset{R^2}{\overset{(S)}{\underset{|}{CH}}}-NH-\underset{R^3}{\overset{(S)}{\underset{|}{CH}}}-COOR^4$$

| Test compounds | | | | ACE-inhibitory activity IC$_{50}$* |
|---|---|---|---|---|
| R$^1$ | R$^2$ | R$^3$ | R$^4$ | (mole/liter) |
| C$_6$H$_5$CH$_2$ | CH$_3$ | C$_6$H$_5$(CH$_2$)$_2$ | H | 1.7 × 10$^{-9}$ |
| " | " | n-C$_8$H$_{17}$ | " | 1.5 × 10$^{-9}$ |
| " | " | (CH$_3$)$_2$CHCH$_2$ | " | 2.1 × 10$^{-9}$ |
| " | " | (CH$_3$)$_2$CH(CH$_2$)$_2$ | " | 3.3 × 10$^{-9}$ |
| " | " | C$_6$H$_5$CH$_2$ | " | 1.1 × 10$^{-8}$ |
| " | C$_2$H$_5$ | C$_6$H$_5$(CH$_2$)$_2$ | " | 2.3 × 10$^{-9}$ |
| " | " | n-C$_8$H$_{17}$ | " | 1.4 × 10$^{-9}$ |
| CH$_3$ | CH$_3$ | C$_6$H$_5$(CH$_2$)$_2$ | " | 1.7 × 10$^{-9}$ |
| " | " | n-C$_8$H$_{17}$ | " | 1.6 × 10$^{-9}$ |

Note:
*: IC$_{50}$ = a dose required to induce 50% inhibition of the ACE activity
(Note: (S) means that the carbon atom has S-configuration)

EXPERIMENT 2

ACE-inhibitory activity in vivo

Normotensive rats and normotensive cats were anesthetized with urethane (1.2 g/kg, s.c.), and angiotensin I (rat: 300 ng/kg, cat: 600 ng/kg) was injected into the jugular vein of the rats and the femoral vein of the cats. The pressor response to angiotensin I was measured with a pressure transducer connected to the carotid artery. Then, a test compound was injected intravenously thereto at a dose of 10 γ/kg, and angiotensin I (rat: 300 ng/kg, cat: 600 ng/kg) was further injected intravenously at intervals. The ACE-inhibitory activity of the test compound was estimated by dose-response curve measured from the pressor responses to angiotensin I which were obtained before and after intravenous injection of the test compound. The results are shown in the following Table 2.

TABLE 2

$$R^1-N\underset{\underset{O}{\|}}{\overset{\overset{(S)}{\overset{|}{\text{COOH}}}}{\diagdown}}N-CO-\underset{R^2}{\overset{(S)}{\underset{|}{C}H}}-NH-\underset{R^3}{\overset{(S)}{\underset{|}{C}H}}-COOR^4$$

| Test compounds | | | | ACE-inhibitory activity (%) | |
|---|---|---|---|---|---|
| $R^1$ | $R^2$ | $R^3$ | $R^4$ | rat | cat |
| $C_6H_5CH_2$ | $CH_3$ | $C_6H_5(CH_2)_2$ | H | 33 ± 4 | 36 ± 8 |
| $CH_3$ | " | " | " | 56 ± 3 | 40 ± 6 |
| " | " | n-$C_8H_{17}$ | " | 47 ± 4 | 36 ± 5 |

(Note: (S) means that the carbon atom has S-configuration)

EXPERIMENT 3

ACE-inhibitory activity in vivo

Normotensive rats were anesthetized with urethane (1.2 g/kg, s.c.), and angiotensin I (300 ng/kg) was injected into the jugular vein of the rats. The pressor response to angiotensin I was measured with a pressure transducer connected to the carotid artery. Then, a test compound was administered orally thereto at a dose of 1 mg/kg, and angiotensin I (300 ng/kg) was further injected intravenously at intervals. The ACE-inhibitory activity of the test compound was estimated from the pressor responses to angiotensin I which were obtained before and after oral administration of the test compound. The results are shown in the following Table 3.

TABLE 3

$$R^1-N\underset{\underset{O}{\|}}{\overset{\overset{(S)}{\overset{|}{\text{COOH}}}}{\diagdown}}N-CO-\underset{R^2}{\overset{(S)}{\underset{|}{C}H}}-NH-\underset{R^3}{\overset{(S)}{\underset{|}{C}H}}-COOR^4$$

| Test compounds | | | | ACE-inhibitory activity (%) |
|---|---|---|---|---|
| $R^1$ | $R^2$ | $R^3$ | $R^4$ | |
| $CH_3$ | $CH_3$ | $C_6H_5(CH_2)_2$ | $C_2H_5$ | 60 ± 6 |
| $CH_3$ | $CH_3$ | n-$C_8H_{17}$ | $C_2H_5$ | 56 ± 7 |

(Note: (S) means that the carbon atom has S-configuration)

EXPERIMENT 4

Hypotensive activity in SHR

A test compound suspended in an aqueous carboxymethyl-cellulose solution was administered orally (dose: 3 mg/kg) to spontaneously hypertensive rats (SHR) fasted overnight. The systolic blood pressure of the rats was measured by the tail plethysmographic technique (The Journal of Laboratory and Clinical Medicine 78 (1971), page 957). The hypotensive activity of the test compound was estimated from the decreased level of blood pressure. The results are shown in the following Table 4.

TABLE 4

$$R^1-N\underset{\underset{O}{\|}}{\overset{\overset{(S)}{\overset{|}{\text{COOH}}}}{\diagdown}}N-CO-\underset{R^2}{\overset{(S)}{\underset{|}{C}H}}-NH-\underset{R^3}{\overset{(S)}{\underset{|}{C}H}}-COOR^4$$

| Test compounds | | | | hypotensive activity | | |
|---|---|---|---|---|---|---|
| | | | | Blood pressure (mm Hg) | | Duration of action |
| $R^1$ | $R^2$ | $R^3$ | $R^4$ | (a) | (b) | (hours) |
| $CH_3$ | $CH_3$ | $C_6H_5(CH_2)_2$ | $C_2H_5$ | 181 ± 3 | 136 ± 4 | >6 |
| $CH_3$ | $CH_3$ | n-$C_8H_{17}$ | $C_2H_5$ | 174 ± 5 | 143 ± 4 | >6 |

Note:
(a): blood pressure measured before administration of the test compound
(b): blood pressure measured after administration of the test compound
(Note: (S) means that the carbon atom has S-configuration)

EXAMPLE 1

(1) 2.4 g of (2S)-2-[N-((1S)-1-ethoxycarbonyl-3-phenylpropyl)amino]propionic acid and 0.99 g of 1-hydroxysuccinimide are dissolved in 40 ml of tetrahydrofuran, and 1.77 g of dicyclohexylcarbodiimide are added thereto at −5° C. to 0° C. under stirring. The mixture is stirred at the same temperature for 30 minutes and further stirred at room temperature overnight. Insoluble materials are filtered off, and the filtrate is concentrated under reduced pressure. 3.24 g of (2S)-2-[N-((1S)-1-ethoxycarbonyl-3-phenylpropyl)amino]propionic acid succinimide ester are thereby obtained as the residue. 2.01 g of benzyl (4S)-1-methyl-2-oxo-imidazolidine-4-carboxylate are dissolved in 30 ml of tetrahydrofuran, and 0.97 g of potassium tert.-butoxide is added thereto at about −40° C. The mixture is stirred at the same temperature for about 5 minutes. A solution of 3.24 g of (2S)-2-[N-((1S)-1-ethoxycarbonyl-3-phenylpropyl)amino]propionic acid succinimide ester in 10 ml of tetrahydrofuran is added to said mixture at −40° C. to −30° C. The mixture is stirred at −30° C. to −10° C. for one hour. 200 ml of ether and 100 ml of water are added to the reaction mixture and the ether layer is collected from the mixture. The ether solution is washed with a saturated sodium chloride solution, dried and concentrated to remove solvent. The residue obtained is purified by silica gel chromatography (solvent, chloroform:ethyl acetate=6:1), whereby 1.87 g of benzyl (4S)-1-methyl-3-{(2S)-2-[N-((1S)-1-ethoxycarbonyl-3-phenylpropyl)amino]propionyl}-2-oxoimidazolidine-4-carboxylate are obtained as colorless viscous oil. Yield: 44.0%

IR $\nu_{max}^{film}$ (cm$^{-1}$): 3320, 1735, 1680

Mass (m/e): 495 (M+)

(2) 1.65 g of benzyl (4S)-1-methyl-3-{(2S)-2-[N-((1S)-1-ethoxycarbonyl-3-phenylpropyl)amino]propionyl}-2-oxo-imidazolidine-4-carboxylate are dissolved in 30 ml of ethanol, and 40 mg of palladium black are added thereto. The mixture is shaken at room temperature in hydrogen gas atmosphere for two hours under an atmospheric pressure. Insoluble materials are filtered off, and the filtrate is concentrated under reduced pressure to remove solvent. The residue is triturated with water, whereby 1.24 g of (4S)-1-methyl-3-{(2S)-2-[N-((1S)-1-ethoxycarbonyl-3-phenylpropyl)amino]propionyl}-2-oxo-imidazolidine-4-carboxylic acid are obtained as colorless crystals. Yield: 91.9%

M.p. 139°–140° C. (recrystallized from a mixture of ethyl acetate and n-hexane)

$[\alpha]_D^{20} -71.7°$ (C=0.5, ethanol)

IR $\nu_{max}^{nujol}$ (cm$^{-1}$): 1720, 1695, 1640, 1610

Mass (m/e): 405 (M+)

EXAMPLE 2

(1) 560 mg of (2S)-2-[N-((1S)-1-ethoxycarbonyl-3-phenylpropyl)amino]propionic acid, 230 mg of 1-hydroxysuccinimide, 413 mg of dicyclohexylcarbodiimide and 400 mg of tert.-butyl (4S)-1-methyl-2-oxo-imidazolidine-4-carboxylate are treated in the same manner as described in Example 1-(1), whereby 650 mg of tert.-butyl (4S)-1-methyl-3-{(2S)-2-[N-((1S)-1-ethoxycarbonyl-3-phenylpropyl)amino]propionyl}-2-oxo-imidazolidine-4-carboxylate are obtained as colorless viscous oil. Yield: 70.4%

IR $\nu_{max}^{film}$ (cm$^{-1}$): 3300, 1730, 1680

Mass (m/e): 461 (M+)

(2) 15 ml of a 13% hydrogen chloride-dioxane solution are added to 462 mg of tert.-butyl (4S)-1-methyl-3-{(2S)-2-[N-((1S)-1-ethoxycarbonyl-3-phenylpropyl)amino]propionyl}-2-oxoimidazolidine-4-carboxylate, and the mixture is allowed to stand at room temperature overnight. The mixture is concentrated under reduced pressure to remove solvent. Ethyl acetate is added to the residue, and the mixture is adjusted to pH 6 with an aqueous sodium bicarbonate solution. The ethyl acetate layer is collected from the mixture, washed with a saturated sodium chloride solution and dried. The ethyl acetate solution is concentrated under reduced pressure to remove solvent. The residue obtained is triturated with n-hexane, whereby 276 mg of (4S)-1-methyl-3-{(2S)-2-[N-((1S)-1-ethoxycarbonyl-3-phenylpropyl)amino]propionyl}-2-oxo-imidazolidine-4-carboxylic acid are obtained as colorless crystals. Yield: 68.1%

The physico-chemical properties of this product are identical with those of the sample obtained in Example 1-(2).

EXAMPLE 3

(1) 2.87 g of (2S)-2-[N-((1S)-1-ethoxycarbonyl)-n-nonyl)amino]propionic acid, 1.15 g of 1-hydroxysuccinimide, 2.06 g of dicyclohexylcarbodiimide and 2.34 g of benzyl (4S)-1-methyl-2-oxo-imidazolidine-4-carboxylate are treated in the same manner as described in Example 1-(1), whereby 2.2 g of benzyl (4S)-1-methyl-3-{(2S)-2-[N-((1S)-1-ethoxycarbonyl-n-nonyl)amino]propionyl}-2-oxo-imidazolidine-4-carboxylate are obtained as colorless viscous oil. Yield: 43.7%

IR $\nu_{max}^{film}$ (cm$^{-1}$): 3320, 1735, 1680

Mass (m/e): 503 (M+)

(2) 1.95 g of benzyl (4S)-1-methyl-3-{(2S)-2-[N-((1S)-1-ethoxycarbonyl-n-nonyl)amino]propionyl}-2-oxo-imidazolidine-4-carboxylate and 50 mg of palladium black are treated in the same manner as described in Example 1-(2), whereby 1.49 g of (4S)-1-methyl-3-{(2S)-2-[N-((1S)-1-ethoxycarbonyl-n-nonyl)amino]propionyl}-2-oxo-imidazolidine-4-carboxylic acid are obtained as colorless crystals. Yield: 93.1%

M.p. 85°–86° C. (recrystallized from a mixture of ethyl acetate and n-hexane)

$[\alpha]_D^{20} -77.5°$ (C=0.5, ethanol)

IR $\nu_{max}^{nujol}$ (cm$^{-1}$): 1730, 1700, 1645, 1610

Mass (m/e): 413 (M+)

EXAMPLE 4

(1) 4.78 g of (2S)-2-[N-((1S)-1-benzyloxycarbonyl-3-phenylpropyl)amino]propionic acid, 1.61 g of 1-hydroxysuccinimide, 2.89 g of dicyclohexylcarbodiimide and 3.28 g of benzyl (4S)-1-methyl-2-oxo-imidazolidine-4-carboxylate are treated in the same manner as described in Example 1-(1). The residue is purified by silica gel chromatography (solvent, toluene:ethyl acetate=4:1), whereby 4.7 g of benzyl (4S)-1-methyl-3-{(2S)-2-[N-((1S)-1-benzyloxycarbonyl-3-phenylpropyl)amino]propionyl}-2-oxo-imidazolidine-4-carboxylate are obtained as colorless viscous oil. Yield: 60.2%

IR $\nu_{max}^{film}$ (cm$^{-1}$): 1735, 1680

Mass (m/e): 557 (M+)

(2) 4.7 g of benzyl (4S)-1-methyl-3-{(2S)-2-[N-((1S)-1-benzyloxycarbonyl-3-phenylpropyl)amino]propionyl]-2-oxo-imidazolidine-4-carboxylate and 300 mg of palladium black are treated in the same manner as described in Example 1-(2), whereby 2.54 g of (4S)-1-methyl-3-{(2S)-2-[N-((1S)-1-carboxy-3-phenylpropyl)amino]propionyl}-2-oxo-imidazolidine-4-carboxylic acid are obtained as colorless crystals. Yield: 79.9%

M.p. 239°–241° C. (decomp.)

$[\alpha]_D^{19} -88.4°$ (C=1, aqueous 5% sodium bicarbonate solution)

IR $\nu_{max}^{nujol}$ (cm$^{-1}$): 1740, 1725, 1690

EXAMPLE 5

(1) 4.54 g of (2S)-2-[N-((1S)-1-benzyloxycarbonyl-n-nonyl)amino]propionic acid, 1.5 g of 1-hydroxysuccinimide, 2.68 g of dicyclohexylcarbodiimide and 3.05 g of benzyl (4S)-1-methyl-2-oxo-imidazolidine-4-carboxylate are treated in the same manner as described in Example 1-(1). The residue is purified by silica gel chromatography (solvent, toluene:ethyl acetate=20:1), whereby 5.25 g of benzyl (4S)-1-methyl-3-{(2S)-2-[N-((1S)-1-benzyloxycarbonyl-n-nonyl)amino]propionyl}-2-oxo-imidazolidine-4-carboxylate are obtained as colorless viscous oil. Yield: 71.3%

IR $\nu_{max}^{film}$ (cm$^{-1}$): 1730, 1680

Mass (m/e): 565 (M+)

(2) 5.17 g of benzyl (4S)-1-methyl-3-{(2S)-2-[N-((1S)-1-benzyloxcarbonyl-n-nonyl)amino]propionyl}-2-oxo-imidazolidine-4-carboxylate and 200 mg of palladium black are treated in the same manner as described in Example 1-(2), whereby 3.26 g of (4S)-1-methyl-3-{(2S)-2-[N-((1S)-1-carboxy-n-nonyl)amino]propionyl}-2-oxo-imidazolidine-4-carboxylic acid are obtained as colorless crystals. Yield: 92.5%

M.p. 204°–205° C. (decomp.) (recrystallized from methanol)

$[\alpha]_D^{19} -84.7°$ (C=1, aqueous 5% sodium bicarbonate solution)

IR $\nu_{max}^{nujol}$ (cm$^{-1}$): 3550, 3150, 1730, 1700

EXAMPLE 6

(1) 2.4 g of (2S)-2-[N-((1S)-1-ethoxycarbonyl-3-phenylpropyl)amino]propionic acid, 0.99 g of 1-hydroxysuccinimide, 1.77 g of dicyclohexylcarbodiimide and 2.67 g of benzyl (4S)-1-benzyl-2-oxo-imidazolidine-4-carboxylate are treated in the same manner as described in Example 1-(1). The residue is purified by silica gel chromatography (solvent, toluene:ethyl acetate=6:1), whereby 2.97 g of benzyl (4S)-1-benzyl-3-{(2S)-2-[N-((1S)-1-ethoxycarbonyl-3-phenylpropyl)amino]propionyl}-2-oxo-imidazolidine-4-carboxylate are obtained as colorless viscous oil. Yield: 60.4%
IR $\nu_{max}^{film}$ (cm$^{-1}$): 3330, 1730, 1680
Mass (m/e): 571 (M+)

(2) 2.6 g of benzyl (4S)-1-benzyl-3-{(2S)-2-[N-((1S)-1-ethoxycarbonyl-3-phenylpropyl)amino]propionyl}-2-oxo-imidazolidine-4-carboxylate and 100 mg of palladium black are treated in the same manner as described in Example 1-(2), whereby 1.97 g of (4S)-1-benzyl-3-{(2S)-2-[N-((1S)-1-ethoxycarbonyl-3-phenylpropyl)amino]propionyl}-2-oxo-imidazolidine-4-carboxylic acid ¼ hydrate are obtained as colorless crystals. Yield: 89.1%
M.p. 56°–57° C.
$[\alpha]_D^{20}$ −53.4° (C=0.5, ethanol)
IR $\nu_{max}^{KBr}$ (cm$^{-1}$): 3450, 1735, 1685
Mass (m/e): 481 (M+)

EXAMPLE 7

(1) 2.87 g of (2S)-2-[N-((1S)-1-ethoxycarbonyl-n-nonyl)amino]propionic acid, 1.15 g of 1-hydroxysuccinimide, 2.06 g of dicyclohexylcarbodiimide and 3.1 g of benzyl (4S)-1-benzyl-2-oxo-imidazolidine-4-carboxylate are treated in the same manner as described in Example 1-(1). The residue is purified by silica gel chromatography (solvent, toluene:ethyl acetate=6:1), whereby 2.97 g of benzyl (4S)-1-benzyl-3-{(2S)-[N-((1S)-1-ethoxycarbonyl-n-nonyl)amino]propionyl}-2-oxo-imidazolidine-4-carboxylate are obtained as colorless viscous oil. Yield: 51.3%
IR $\nu_{max}^{film}$ (cm$^{-1}$): 3320, 1730, 1690
Mass (m/e): 579 (M+)

(2) 2.7 g of benzyl (4S)-1-benzyl-3-{(2S)-2-[N-((1S)-1-ethoxycarbonyl-n-nonyl)amino]propionyl}-2-oxo-imidazolidine-4-carboxylate and 100 mg of palladium black are treated in the same manner as described in Example 1-(2), whereby 2.05 g of (4S)-1-benzyl-3-{(2S)-2-[N-((1S)-1-ethoxycarbonyl-n-nonyl)amino]propionyl}-2-oxo-imidazolidine-4-carboxylic acid are obtained as colorless crystals. Yield: 89.9%
M.p. 86°–88° C.
$[\alpha]_D^{20}$ −59.7° (C=0.5, ethanol)
IR $\nu_{max}^{nujol}$ (cm$^{-1}$): 1730, 1695, 1645, 1610
Mass (m/e): 489 (M+)

EXAMPLE 8

(1) 4.1 g of (2S)-2-[N-((1S)-1-benzyloxycarbonyl-3-phenylpropyl)amino]propionic acid, 1.38 g of 1-hydroxysuccinimide, 2.48 g of dicyclohexylcarbodiimide and 3.72 g of benzyl (4S)-1-benzyl-2-oxo-imidazolidine-4-carboxylate are treated in the same manner as described in Example 1-(1). The residue is purified by silica gel chromatography (solvent, toluene:ethyl acetate=8:1), whereby 5.47 g of benzyl (4S)-1-benzyl-3-{(2S)-2-[N-((1S)-1-benzyloxycarbonyl-3-phenylpropyl)amino]propionyl}-2-oxo-imidazolidine-4-carboxylate are obtained as colorless viscous oil. Yield: 71.9%
IR $\nu_{max}^{film}$ (cm$^{-1}$): 1730, 1680
Mass (m/e): 633 (M+)

(2) 5.4 g of benzyl (4S)-1-benzyl-3-{(2S)-2-[N-((1S)-1-benzyloxycarbonyl-3-phenylpropyl)amino]propionyl}-2-oxo-imidazolidine-4-carboxylate and 300 mg of palladium black are treated in the same manner as described in Example 1-(2), whereby 3.23 g of (4S)-1-benzyl-3-{(2S)-2-[N-((1S)-1-carboxy-3-phenylpropyl)amino]propionyl}-2-oxo-imidazolidine-4-carboxylic acid are obtained as colorless crystals. Yield: 83.6%
M.p. 223°–225° C. (decomp.)
$[\alpha]_D^{19}$ −62.7° (C=1, aqueous 5% sodium bicarbonate solution)
IR $\nu_{max}^{nujol}$ (cm$^{-1}$): 3150, 1740, 1700

EXAMPLE 9

(1) 3.5 g of (2S)-2-[N-((1S)-1-benzyloxycarbonyl-n-nonyl)amino]propionic acid, 1.5 g of 1-hydroxysuccinimide, 2.06 g of dicyclohexylcarbodiimide and 3.01 g of benzyl (4S)-1-benzyl-2-oxo-imidazolidine-4-carboxylate are treated in the same manner as described in Example 1-(1). The residue is purified by silica gel chromatography (solvent, toluene:ethyl acetate=20:1), whereby 4.5 g of benzyl (4S)-1-benzyl-3-{(2S)-2-[N-((1S)-1-benzyloxycarbonyl-n-nonyl)amino]propionyl}-2-oxo-imidazolidine-4-carboxylate are obtained as colorless viscous oil. Yield: 70.2%
IR $\nu_{max}^{film}$ (cm$^{-1}$): 1730, 1680

(2) 4.3 g of benzyl (4S)-1-benzyl-3-{(2S)-2-[N-((1S)-1-benzyloxycarbonyl-n-nonyl)amino]propionyl}-2-oxo-imidazolidine-4-carboxylate and 200 mg of palladium black are treated in the same manner as described in Example 1-(2), whereby 2.81 g of (4S)-1-benzyl-3-{(2S)-2-[N-((1S)-1-carboxy-n-nonyl)amino]propionyl}-2-oxo-imidazolidine-4-carboxylic acid are obtained as colorless crystals. Yield: 90.9%
M.p. 211°–215° C. (decomp.) (recrystallized from methanol) $[\alpha]_D^{19}$ −64.3° (C=1, aqueous 5% sodium bicarbonate solution)
IR $\nu_{max}^{nujol}$ (cm$^{-1}$): 3150, 1740, 1710

EXAMPLE 10

(1) 7.5 g of tert.-butyl (4S)-1-benzyl-2-oxo-imidazolidine-4-carboxylate are dissolved in 70 ml of tetrahydrofuran, and 3.1 g of potassium tert.-butoxide are added thereto at about −40° C. The mixture is stirred at the same temperature for 10 minutes. A solution of 6.7 g of 2-bromopropionyl chloride in 10 ml of tetrahydrofuran is added dropwise to said mixture and stirred at −40° C. to −20° C. for about 1.5 hours. Ether is added to the reaction mixture, and the mixture is washed with an aqueous diluted acetic acid solution, an aqueous sodium bicarbonate solution and a saturated sodium chloride solution, succesively. The resultant solution is dried and concentrated to remove solvent, whereby 9.5 g of tert.-butyl (4S)-1-benzyl-3-(2-bromopropionyl)-2-oxo-imidazolidine-4-carboxylate are obtained as colorless crystalline residue. Yield: 85.1%
IR $\nu_{max}^{nujol}$ (cm$^{-1}$): 1735, 1690, 1675

(2) A mixture of 8.9 g of tert.-butyl (4S)-1-benzyl-3-(2-bromopropionyl)-2-oxo-imidazolidine-4-carboxylate, 5.9 g of benzyl (2S)-2-amino-4-phenylbutyrate, 3.0 g of anhydrous potassium carbonate and 20 ml of hexamethylphosphoric triamide is vigorously stirred at room temperature for 2 days. Ethyl acetate and water are added to the reaction mixture. The organic layer is collected therefrom, dried and concentrated to remove solvent. The residue is chromatographed on silica gel column (solvent, toluene:ethyl acetate=6:1), whereby tert-butyl (4S)-1-benzyl-3-{(2S)-2-[N-((1S)-1-benzyloxycarbonyl-3-phenylpropyl)amino]propionyl}-2-oxo-imidazolidine-4-carboxylate (α-isomer) and tert.-butyl (4S)-1-benzyl-3-{(2R)-2-[N-((1S)-1-benzyloxycarbonyl-3-phenylpropyl)amino]propionyl}-2-oxo-imidazolidine-4-carboxylate (β-isomer) are obtained, respectively.
α-isomer:
colorless viscous oil Yield: 1.4 g (10.1%)
IR $\nu_{max}^{film}$ (cm$^{-1}$): 3300, 1725, 1680
Mass (m/e): 599 (M+)

β-isomer:
colorless viscous oil Yield: 8.4 g (60.4%)
IR $\nu_{max}^{film}$ (cm$^{-1}$): 3300, 1725, 1680
Mass (m/e): 599 (M+)

(3) 20 ml of a 13% hydrogen chloride-dioxane solution are added to 1.2 g of tert.-butyl (4S)-1-benzyl-3-{(2S)-2-[N-((1S)-1-benzyloxycarbonyl-3-phenylpropyl)amino]propionyl}-2-oxo-imidazolidine-4-carboxylate, and the mixture is allowed to stand at room temperature overnight. The mixture is concentrated under reduced pressure to remove solvent. Ethyl acetate and water are added to the residue and the mixture is adjusted to pH 5 to 6 with an aqueous sodium bicarbonate solution. The ethyl acetate layer is collected therefrom, washed with a saturated sodium chloride solution and dried. The resultant solution is concentrated under reduced pressure to remove solvent, whereby 1.0 g of (4S)-1-benzyl-3-{(2S)-2-[N-((1S)-1-benzyloxycarbonyl-3-phenylpropyl)amino]propionyl}-2-oxo-imidazolidine-4-carboxylic acid is obtained as colorless viscous oil. Yield: 91.9%

(4) 100 ml of a 13% hydrogen chloride-dioxane solution are added to 8.0 g of tert.-butyl (4S)-1-benzyl-3-{(2R)-2-[N-((1S)-1-benzyloxycarbonyl-3-phenylpropyl)amino]propionyl}-2-oxo-imidazolidine-4-carboxylate, and the mixture is allowed to stand at room temperature overnight. The mixture is concentrated under reduced pressure to remove solvent. The residue is triturated with ether, whereby 7.2 g of (4S)-1-benzyl-3-{(2R)-2-[N-((1S)-1-benzyloxycarbonyl-3-phenylpropyl)amino]propionyl}-2-oxo-imidazolidine-4-carboxylic acid hydrochloride are obtained as colorless crystals. Yield: 93.0%
M.p. 202°–203° C.
IR $\nu_{max}^{nujol}$ (cm$^{-1}$): 1760, 1740, 1680

(5) 1.0 g of (4S)-1-benzyl-3-{(2S)-2-[N-((1S)-1-benzyloxycarbonyl-3-phenylpropyl)amino]propionyl}-2-oxo-imidazolidine-4-carboxylic acid is dissolved in 20 ml of methanol, and 50 mg of palladium black are added thereto. The mixture is shaken at room temperature in hydrogen gas atmosphere for two hours under an atmospheric pressure. Insoluble materials are filtered off, and the filtrate is concentrated under reduced pressure to remove solvent. The residue is triturated with ether, whereby 0.7 g of (4S)-1-benzyl-3-{(2S)-2-[N-((1S)-1-carboxy-3-phenylpropyl)amino]propionyl}-2-oxo-imidazolidine-4-carboxylic acid is obtained as colorless crystals. Yield: 83.9% The physico-chemical properties of this product are identical with those of the sample obtained in Example 8-(2).

(6) 3.5 g of (4S)-1-benzyl-3-{(2R)-2-[N-((1S)-1-benzyloxycarbonyl-3-phenylpropyl)amino]propionyl}-2-oxo-imidazolidine-4-carboxylic acid hydrochloride are dissolved in 50 ml of methanol, and 100 mg of palladium black are added thereto. The mixture is shaken at room temperature in hydrogen gas atmosphere for two hours under an atmospheric pressure. Insoluble materials are filtered off, and the filtrate is concentrated under reduced pressure to remove solvent. The residue is triturated with water, whereby 2.65 g of (4S)-1-benzyl-3-{(2R)-2-[N-((1S)-1-carboxy-3-phenylpropyl)amino]propionyl}-2-oxo-4-carboxylic acid hydrochloride are obtained as colorless crystals. Yield: 89.6%
M.p. 164°–165° C. (decomp.)
$[\alpha]_D^{27}$ +65.8° (C=0.8, aqueous 75% methanol-containing 1% hydrogen chloride)
IR $\nu_{max}^{nujol}$ (cm$^{-1}$): 3600, 3500, 1740, 1695

EXAMPLE 11

(1) A mixture of 3.7 g of tert.-butyl (4S)-1-benzyl-3-(2-bromopropionyl)-2-oxo-imidazolidine-4-carboxylate, 2.5 g of benzyl (2S)-2-amino-n-decanoate, 1.4 g of anhydrous potassium carbonate and 8 ml of hexamethylphosphoric triamide is treated in the same manner as described in Example 10-(2). The residue is chromatographed on silica gel column (solvent, chloroform:ethyl acetate=25:1), whereby tert.-butyl (4S)-1-benzyl-3-{(2S)-2-[N-((1S)-1-benzyloxycarbonyl-n-nonyl)amino]propionyl}-2-oxo-imidazolidine-4-carboxylate (α-isomer) and tert.-butyl (4S)-1-benzyl-3-{(2R)-2-[N-((1S)-1-benzyloxycarbonyl-n-nonyl)amino]propionyl}-2-oxo-imidazolidine-4-carboxylate (β-isomer) are obtained, respectively.
α-isomer:
colorless viscous oil Yield: 0.6 g (11.0%)
IR $\nu_{max}^{film}$ (cm$^{-1}$): 3320, 1735, 1680
Mass (m/e): 607 (M+)
β-isomer:
colorless viscous oil Yield: 4.5 g (82.3%)
IR $\nu_{max}^{film}$ (cm$^{-1}$): 3320, 1735, 1685
Mass (m/e): 607 (M+)

(2) 0.5 g of tert.-butyl (4S)-1-benzyl-3-{(2S)-2-[N-((1S)-1-benzyloxycarbonyl-n-nonyl)amino]propionyl}-2-oxo-imidazolidine-4-carboxylate and 20 ml of a 13% hydrogen chloride-dioxane solution are treated in the same manner as described in Example 10-(3), whereby 0.4 g of (4S)-1-benzyl-3-{(2S)-2-[N-((1S)-1-benzyloxycarbonyl-n-nonyl)amino]propionyl}-2-oxo-imidazolidine-4-carboxylic acid is obtained as colorless viscous oil. This oil (0.4 g) and 15 mg of palladium black are treated in the same manner as described in Example 10-(5), whereby 0.2 g of (4S)-1-benzyl-3-{(2S)-2-[N-((1S)-1-carboxy-n-nonyl)amino]propionyl}-2-oxo-imidazolidine-4-carboxylic acid is obtained as colorless crystals. The physico-chemical properties of this product are identical with those of the sample obtained in Example 9-(2).

(3) 3.5 g of tert.-butyl (4S)-1-benzyl-3-{(2R)-2-[N-((1S)-1-benzyloxycarbonyl-n-nonyl)amino]propionyl}-2-oxo-imidazolidine-4-carboxylate and 40 ml of a 13% hydrogen chloride-dioxane solution are treated in the same manner as described in Example 10-(3), whereby 2.9 g of (4S)-1-benzyl-3-{(2R)-2-[N-((1S)-1-benzyloxycarbonyl-n-nonyl)amino]propionyl}-2-oxo-imidazolidine-4-carboxylic acid are obtained as colorless viscous oil. This oil (2.9 g) and 100 mg of palladium black are treated in the same manner as described in Example 10-(5), whereby 2.2 g of (4S)-1-benzyl-3-{(2R)-2-[N-((1S)-1-carboxy-n-nonyl)amino]propionyl}-2-oxo-imidazolidine-4-carboxylic acid are obtained as colorless crystals. Yield: 82.8%
M.p. 123°–127° C.
$[\alpha]_D^{25}$ +28.3° (C=1, 1N hydrochloric acid-methanol=1:4)
IR $\nu_{max}^{nujol}$ (cm$^{-1}$): 1740, 1705

EXAMPLE 12

(1) A mixture of 5.2 g of tert.-butyl (4S)-1-benzyl-3-(2-bromopropionyl)-2-oxo-imidazolidine-4-carboxylate, 2.8 g of benzyl (2S)-2-amino-4-methyl-pentanoate, 1.8 g of anhydrous potassium carbonate and 8 ml of hexamethylphosphoric triamide is treated in the same manner as described in Example 10-(2).The residue is chromatographed on silica gel column (solvent, chloroform:ethyl acetate=15:1), whereby tert.-butyl (4S)-1-benzyl-3-

{(2S)-2-[N-((1S)-1-benzyloxycarbonyl-isopentyl-)amino]propionyl}-2-oxo-imidazolidine-4-carboxylate (α-isomer) and tert.-butyl (4S)-1-benzyl-3-{(2R)-2-[N-((1S)-1-benzyloxycarbonyl-isopentyl)amino]propionyl}-2-oxo-imidazolidine-4-carboxylate (β-isomer) are obtained, respectively.

α-isomer:
colorless viscous oil Yield: 0.75 g (10.8%)
IR $\nu_{max}^{film}$ (cm$^{-1}$): 3320, 1735, 1680
Mass (m/e): 551 (M+)

β-isomer:
colorless viscous oil Yield: 4.6 g (65.9%)
IR $\nu_{max}^{film}$ (cm$^{-1}$): 3320, 1735, 1685
Mass (m/e): 551 (M+)

(2) 0.7 g of tert.-butyl (4S)-1-benzyl-3-{(2S)-2-[N-((1S)-1-benzyloxycarbonyl-isopentyl)amino]propionyl}-2-oxo-imidazolidine-4-carboxylate and 20 ml of a 13% hydrogen chloride-dioxane solution are treated in the same manner as described in Example 10-(3), whereby 0.55 g of (4S)-1-benzyl-3-{(2S)-2-[N-((1S)-1-benzyloxycarbonyl-isopentyl)amino]propionyl}-2-oxo-imidazolidine-4-carboxylic acid is obtained as colorless viscous oil. This oil (0.55 g) and 20 mg of palladium black are treated in the same manner as described in Example 10-(5), whereby 0.35 g of (4S)-1-benzyl-3-{(2S)-2-[N-((1S)-1-carboxy-isopentyl)amino]propionyl}-2-oxo-imidazolidine-4-carboxylic acid is obtained as colorless cyrstals. Yield: 68% This product begins to gradually decompose at about 141° C.

IR $\nu_{max}^{nujol}$ (cm$^{-1}$): 1735, 1685, 1615

(3) 3.2 g of tert.-butyl (4S)-1-benzyl-3-{(2R)-2-[N-((1S)-1-benzyloxycarbonyl-isopentyl)amino]propionyl}-2-oxo-imidazolidine-4-carboxylate and 50 ml of a 13% hydrogen chloride-dioxane solution are treated in the same manner as described in Example 10-(3), whereby 2.3 g of (4S)-1-benzyl-3-{(2R)-2-[N-((1S)-1-benzyloxycarbonyl-isopentyl)amino]propionyl}-2-oxo-imidazolidine-4-carboxylic acid are obtained as colorless viscous oil. This oil (2.3 g) and 80 mg of palladium black are treated in the same manner as described in Example 10-(5), whereby 1.5 g of (4S)-1-benzyl-3-{(2R)-2-[N-((1S)-1-carboxy-isopentyl)amino]propionyl}-2-oxo-imidazolidine-4-carboxylic acid are obtained as colorless crystals. Yield: 63.8% This product begins to gradually decompose at about 140° C.

IR $\nu_{max}^{nujol}$ (cm$^{-1}$): 1725, 1700, 1600

EXAMPLE 13

(1) A mixture of 5.0 g of tert.-butyl (4S)-1-benzyl-3-(2-bromopropionyl)-2-oxo-imidazolidine-4-carboxylate, 2.9 g of benzyl (2S)-2-amino-5-methyl-n-hexanoate, 2.0 g of anhyrous potassium carbonate and 8 ml of hexamethylphosphoric triamide is treated in the same manner as described in Example 10-(2). The residue is chromatographed on silica gel column (solvent, chloroform: ethyl acetate = 15:1), whereby tert.-butyl (4S)-1-benzyl-3-{(2S)-2-[N-((1S)-1-benzyloxycarbonyl-4-methyl-n-pentyl)amino]propionyl}-2-oxo-imidazolidine-4-carboxylate (α-isomer) and tert.-butyl (4S)-1-benzyl-3-{(2R)-2-[N-((1S)-1-benzyloxycarbonyl-4-methyl-n-pentyl)amino]propionyl}-2-oxo-imidazolidine-4-carboxylate (β-isomer) are obtained, respectively.

α-isomer:
colorless viscous oil Yield: 1.3 g (18.9%)
IR $\nu_{max}^{film}$ (cm$^{-1}$): 3320, 1735, 1685
Mass (m/e): 565 (M+)

β-isomer:
colorless viscous oil Yield: 4.8 g (69.8%)
IR $\nu_{max}^{film}$ (cm$^{-1}$): 3320, 1740, 1685
Mass (m/e): 565 (M+)

(2) 1.2 g of tert.-butyl (4S)-1-benzyl-3-{(2S)-2-[N-((1S)-1-benzyloxycarbonyl-4-methyl-n-pentyl)amino]propionyl}-2-oxo-imidazolidine-4-carboxylate and 30 ml of a 13% hydrogen chloride-dioxane solution are treated in the same manner as described in Example 10-(3), whereby 1.0 g of (4S)-1-benzyl-3-{(2S)-2-[N-((1S)-1-benzyloxycarbonyl-4-methyl-n-pentyl)amino]propionyl}-2-oxo-imidazolidine-4-carboxylic acid is obtained as colorless viscous oil. This oil (1.0 g) and 50 mg of palladium black are treated in the same manner as described in Example 10-(5), whereby 0.75 g of (4S)-1-benzyl-3-{(2S)-2-[N-((1S)-1-carboxy-4-methyl-n-pentyl)amino]propionyl}-2-oxo-imidazolidine-4-carboxylic acid is obtained as colorless crystals. Yield: 84.3%

M.p. 208°-209° C. (decomp.)
IR $\nu_{max}^{nujol}$ (cm$^{-1}$): 1740, 1700, 1620

(3) 3.2 g of tert.-butyl (4S)-1-benzyl-3-{(2R)-2-[N-((1S)-1-benzyloxycarbonyl-4-methyl-n-pentyl)amino]propionyl}-2-oxo-imidazolidine-4-carboxylate and 50 ml of a 13% hydrogen chloride-dioxane solution are treated in the same manner as described in Example 10-(3), whereby 2.6 g of (4S)-3-{(2R)-2-[N-((1S)-1-benzyloxycarbonyl-4-methyl-n-pentyl)amino]propionyl}-2-oxo-imidazolidine-4-carboxylic acid are obtained as colorless viscous oil. This oil (2.6 g) and 120 mg of palladium black are treated in the same manner as described in Example 10-(5), whereby 2.05 g of (4S)-1-benzyl-3-{(2R)-2-[N-((1S)-1-carboxy-4-methyl-n-pentyl)amino]propionyl}-2-oxo-imidazolidine-4-carboxylic acid are obtained as colorless crystals. Yield: 86.4%

M.p. 129°-130° C. (decomposed gradually)
IR $\nu_{max}^{nujol}$ (cm$^{-1}$): 1725, 1700, 1600

EXAMPLE 14

(1) 5.5 g of tert.-butyl (4S)-1-benzyl-2-oxo-imidazolidine-4-carboxylate, 2.54 g of 2-chloropropionyl chloride, 2.25 g of potassium tert.-butoxide and 60 ml of tetrahydrofuran are treated in the same manner as described in Example 10-(1), whereby 5.0 g of tert.-butyl (4S)-1-benzyl-3-(2-chloropropionyl)-2-oxo-imidazolidine-4-carboxylate are obtained as colorless crystals. Yield: 68.5%

IR $\nu_{max}^{nujol}$ (cm$^{-1}$): 1735, 1680

(2) A mixture of 4.5 g of tert.-butyl (4S)-1-benzyl-3-(2-chloropropionyl)-2-oxo-imidazolidine-4-carboxylate, 3.2 g of benzyl (2S)-2-amino-3-phenylpropionate, 2.5 g of anhydrous potassium carbonate, 20 ml of hexamethylphosphoric triamide and 20 mg of potassium iodide is treated in the same manner as described in Example 10-(2). The residue is chromatographed on silica gel column (solvent, toluene:ethyl acetate = 10:1), whereby tert.-butyl (4S)-1-benzyl-3-{(2S)-2-[N-((1S)-1-benzyloxycarbonyl-2-phenylethyl)amino]propionyl}-2-oxo-imidazolidine-4-carboxylate (α-isomer) and tert.-butyl (4S)-1-benzyl-3-{(2R)-2-[N-((1S)-1-benzyloxycarbonyl-2-phenylethyl)amino]-propionyl}-2-oxo-imidazolidine-4-carboxylate (β-isomer) are obtained, respectively.

α-isomer:
colorless viscous oil Yield: 0.7 g (9.7%)
IR $\nu_{max}^{film}$ (cm$^{-1}$): 3450, 3330, 1750, 1720, 1680
Mass (m/e): 585 (M+)

β-isomer:
colorless viscous oil Yield: 3.9 g (54.3%)
IR $\nu_{max}^{film}$ (cm$^{-1}$): 3450, 3300, 1750, 1720, 1680
Mass (m/e): 585 (M+)

(3) 0.6 g of tert.-butyl (4S)-1-benzyl-3-{(2S)-2-[N-((1S)-1-benzyloxycarbonyl-2-phenylethyl)amino]propionyl}-2-oxo-imidazolidine-4-carboxylate and 20 ml of a 20% hydrogen chloride-dioxane solution are treated in the same manner as described in Example 10-(3), whereby 0.47 g of (4S)-1-benzyl-3-{(2S)-2-[N-((1S)-1-benzyloxycarbonyl-2-phenylethyl)amino]propionyl}-2-oxo-imidazolidine-4-carboxylic acid is obtained as colorless viscous oil. This oil (0.47 g) and 30 mg of palladium black are treated in the same manner as described in Example 10-(5), whereby 0.32 g of (4S)-1-benzyl-3-{(2S)-2-[N-((1S)-1-carboxy-2-phenylethyl)amino]propionyl}-2-oxo-imidazolidine-4-carboxylic acid is obtained as colorless crystals. Yield: 71.1%

M.p. 184°–185° C. (decomp.)
$[\alpha]_D^{26}$ −50.4° (C=0.5, methanol)
IR $\nu_{max}^{nujol}$ (cm$^{-1}$): 3350, 1735, 1690

(4) 3.6 g of tert.-butyl (4S)-1-benzyl-3-{(2R)-2-[N-((1S)-1-benzyloxycarbonyl-2-phenylethyl)amino]propionyl}-2-oxo-imidazolidine-4-carboxylate and 40 ml of a 10% hydrogen chloride-dioxane solution are treated in the same manner as described in Example 10-(5), whereby 2.6 g of (4S)-1-benzyl-3-{(2R)-2-[N-((1S)-1-benzyloxycarbonyl-2-phenylethyl)amino]propionyl}-2-oxo-imidazolidine-4-carboxylic acid are obtained as colorless viscous oil. This oil (2.6 g) and 100 mg of palladium black are treated in the same manner as described in Example 10-(5), whereby 1.85 g of (4S)-1-benzyl-3-{(2R)-2-[N-((1S)-1-carboxy-2-phenylethyl)amino]propionyl}-2-oxo-imidazolidine-4-carboxylic acid are obtained as colorless crystals. Yield: 68.5%

M.p. 125°–130° C. (decomp.)
$[\alpha]_D^{26}$ −4.4° (C=0.5, methanol)
IR $\nu_{max}^{nujol}$ (cm$^{-1}$): 3350, 1730, 1695

EXAMPLE 15

(1) 7.5 g of tert.-butyl (4S)-1-benzyl-2-oxo-imidazolidine-4-carboxylate, 5.1 g of 2-bromo-n-butyryl chloride, 3.1 g of potassium tert.-butoxide and 80 ml of tetrahydrofuran are treated in the same manner as described in Example 10-(1), whereby 8.0 g of tert.-butyl (4S)-1-benzyl-3-(2-bromo-n-butyryl)-2-oxo-imidazolidine-4-carboxylate are obtained as colorless crystals. Yield: 69.3%

M.p. 105°–107° C.
IR $\nu_{max}^{nujol}$ (cm$^{-1}$): 1730, 1690

(2) A mixture of 5.0 g of tert.-butyl (4S)-1-benzyl-3-(2-bromo-n-butyryl)-2-oxo-imidazolidine-4-carboxylate, 3.3 g of benzyl (2S)-2-amino-n-decanoate, 2.0 g of anhydrous potassium carbonate and 15 ml of hexamethylphosphoric triamide is treated in the same manner as described in Example 10-(2). The residue is chromatographed on silica gel column (solvent, chloroform:ethyl acetate=30:1), whereby tert.-butyl (4S)-1-benzyl-3-{(2S)-2-[N-((1S)-1-benzyloxycarbonyl-n-nonyl)amino]-n-butyryl}-2-oxo-imidazolidine-4-carboxylate (α-isomer) and tert.-butyl (4S)-1-benzyl-3-{(2R)-2-[N-((1S)-1-benzyloxycarbonyl-n-nonyl)amino]-n-butyryl}-2-oxo-imidazolidine-4-carboxylate (β-isomer) are obtained, respectively.

α-isomer:
colorless viscous oil Yield: 0.25 g (3.4%)
IR $\nu_{max}^{film}$ (cm$^{-1}$): 1740, 1680
β-isomer:
colorless viscous oil Yield: 4.4 g (60.2%)
IR $\nu_{max}^{film}$ (cm$^{-1}$): 1740, 1680

(3) 0.2 g of tert.-butyl (4S)-1-benzyl-3-{(2S)-2-[N-((1S)-1-benzyloxycarbonyl-n-nonyl)amino]-n-butyryl}-2-oxo-imidazolidine-4-carboxylate and 10 ml of a 13% hydrogen chloride-dioxane solution are treated in the same manner as described in Example 10-(3), whereby 0.17 g of (4S)-1-benzyl-3-{(2S)-2-[N-((1S)-1-benzyloxycarbonyl-n-nonyl)amino]-n-butyryl}-2-oxo-imidazolidine-4-carboxylic acid is obtained as colorless viscous oil. This oil (0.17 g) and 8 mg of palladium black are treated in the same manner as described in Example 10-(5), whereby 0.13 g of (4S)-1-benzyl-3-{(2S)-2-[N-((1S)-1-carboxy-n-nonyl)amino]-n-butyryl}-2-oxo-imidazolidine-4-carboxylic acid is obtained as colorless crystals. Yield: 85%

M.p. 175°–185° C. (decomp.)
IR $\nu_{max}^{nujol}$ (cm$^{-1}$): 1740, 1680

(4) 4.0 g of tert.-butyl (4S)-1-benzyl-3-{(2R)-2-[N-((1S)-1-benzyloxycarbonyl-n-nonyl)amino]-n-butyryl}-2-oxo-imidazolidine-4-carboxylate and 50 ml of a 13% hydrogen chloride-dioxane solution are treated in the same manner as described in Example 10-(3), whereby 3.0 g of (4S)-1-benzyl-3-{(2R)-2-[N-((1S)-1-benzyloxycarbonyl-n-nonyl)amino]-n-butyryl}-2-oxo-imidazolidine-4-carboxylic acid are obtained as colorless viscous oil. This oil (3.0 g) and 150 mg of palladium black are treated in the same manner as described in Example 10-(5), whereby 1.85 g of (4S)-1-benzyl-3-{(2R)-2-[N-((1S)-1-carboxy-n-nonyl)amino]-n-butyryl}-2-oxo-imidazolidine-4-carboxylic acid are obtained as colorless crystals. Yield: 60.5%

M.p. 95°–105° C. (decomp.)
$[\alpha]_D^{26}$ +50.2° (C=1, methanol)
IR $\nu_{max}^{nujol}$ (cm$^{-1}$): 1735, 1685

EXAMPLE 16

(1) 5.0 g of tert.-butyl (4S)-1-methyl-2-oxo-imidazolidine-4-carboxylate, 4.7 g of 2-bromo-n-butyryl chloride, 2.8 g of potassium tert.-butoxide and 60 ml of tetrahydrofuran are treated in the same manner as described in Example 10-(1), whereby 7.0 g of tert.-butyl (4S)-1-methyl-3-(2-bromo-n-butyryl)-2-oxo-imidazolidine-4-carboxylate are obtained as colorless crystals. Yield: 80.3%

M.p. 61°–62° C.

(2) A mixture of 6.7 g of tert.-butyl (4S)-1-methyl-3-(2-bromo-n-butyryl)-2-oxo-imidazolidine-4-carboxylate, 5.4 g of benzyl (2S)-2-amino-n-decanoate, 3.0 g of anhydrous potassium carbonate and 15 ml of hexamethylphosphoric triamide is treated in the same manner as described in Example 10-(2). The residue is chromatographed on silica gel column (solvent, chloroform:ethyl acetate=30:1), whereby tert.-butyl (4S)-1-methyl-3-{(2S)-2-[N-((1S)-1-benzyloxycarbonyl-n-nonyl)amino]-n-butyryl}-2-oxo-imidazolidine-4-carboxylate (α-isomer) and tert.-butyl (4S)-1-methyl-3-{(2R)-2-[N-((1S)-1-benzyloxycarbonyl-n-nonyl)amino]-n-butyryl}-2-oxo-imidazolidine-4-carboxylate (β-isomer) are obtained, respectively.

α-isomer:
colorless viscous oil Yield: 0.15 g (1.4%)
IR $\nu_{max}^{film}$ (cm$^{-1}$): 1740, 1680
Mass (m/e): 545 (M+)
β-isomer:
colorless viscous oil Yield: 2.2 g (21.0%)
IR $\nu_{max}^{film}$ (cm$^{-1}$): 1740, 1680
Mass (m/e): 545 (M+)

(3) 0.12 g of tert.-butyl (4S)-1-methyl-3-{(2S)-2-[N-(1S)-1-benzyloxycarbonyl-n-nonyl)amino]-n-butyryl}-2-oxo-imidazolidine-4-carboxylate and 10 ml of a 13% hydrogen chloried-dioxane solution are treated in the same manner as described in Example 10-(3). Then, the resultant product and 5 mg of palladium black are treated in the same manner as described in Example 10-(5), whereby 0.08 g of (4S)-1-methyl-3-{(2S)-2-[N-((1S)-1-carboxy-n-nonyl)amino]-n-butyryl}-2-oxo-imidazolidine-4-carboxylic acid is obtained as colorless crystals. Yield: 91.1%

M.p. 90°–110° C. (decomp.)

IR $\nu_{max}^{nujol}$ (cm$^{-1}$): 1740, 1680

(4) 2.0 g of tert.-butyl (4S)-1-methyl-3-{(2R)-2-[N-((1S)-1-benzyloxycarbonyl-n-nonyl)amino]-n-butyryl}-2-oxo-imidazolidine-4-carboxylate and 20 ml of a 13% hydrogen chloride-dioxane solution are treated in the same manner as described in Example 10-(3). Then, the resultant product and 100 mg of palladium black are treated in the same manner as described in Example 10-(5), whereby 1.0 g of (4S)-1-methyl-3-{(2R)-2-[N-((1S)-1-carboxy-n-nonyl)amino]-n-butyryl}-2-oxo-imidazolidine-4-carboxylic acid is obtained as colorless crystals. Yield: 68.3%

M.p. 115°–140° C. (decomp.)

$[\alpha]_D^{26}$ −13.0° (C=1, 1N hydrochloric acid:methanol=4:1)

IR $\nu_{max}^{nujol}$ (cm$^{-1}$): 1740, 1680

EXAMPLE 17

(1) A mixture of 6.8 g of tert.-butyl (4S)-1-benzyl-3-(2-bromo-n-butyryl)-2-oxo-imidazolidine-4-carboxylate, 4.3 g of benzyl (2S)-2-amino-4-phenyl-n-butyrate, 2.4 g of anhydrous potassium carbonate and 12 ml of hexamethylphosphoric triamide is treated in the same manner as described in Example 10-(2). The residue is chromatographed on silica gel column (solvent, chloroform:ethyl acetate=30:1), whereby tert.-butyl (4S)-1-benzyl-3-{(2S)-2-[N-((1S)-1-benzyloxycarbonyl-3-phenylpropyl)amino]-n-butyryl}-2-oxo-imidazolidine-4-carboxylate (α-isomer) and tert.-butyl (4S)-1-benzyl-3-{(2R)-2-[N-((1S)-1-benzyloxycarbonyl-3-phenylpropyl)amino]-n-butyryl}-2-oxo-imidazolidine-4-carboxylate (β-isomer) are obtained, respectively.

α-isomer:
colorless viscous oil Yield: 0.2 g (2.0%)
IR $\nu_{max}^{film}$ (cm$^{-1}$): 3320, 1755, 1680
Mass (m/e): 613 (M$^+$)

β-isomer:
colorless viscous oil Yield: 2.4 g (24.5%)
IR $\nu_{max}^{film}$ (cm$^{-1}$): 3320, 1735, 1680
Mass (m/e): 613 (M$^+$)

(2) 0.15 g of tert.-butyl (4S)-1-benzyl-3-{(2S)-2-[N-((1S)-1-benzyloxycarbonyl-3-phenylpropyl)amino]-n-butyryl}-2-oxo-imidazolidine-4-carboxylate and 10 ml of a 13% hydrogen chloride-dioxane solution are treated in the same manner as described in Example 10-(3), whereby 0.13 g of (4S)-1-benzyl-3-{(2S)-2-[N-((1S)-1-benzyloxycarbonyl-3-phenylpropyl)amino]-n-butyryl}-2-oxoimidazolidine-4-carboxylic acid is obtained as colorless viscous oil. This oil (0.13 g) and 8 mg of palladium black are treated in the same manner as described in Example 10-(5), whereby 0.1 g of (4S)-1-benzyl-3-{(2S)-2-[N-((1S)-1-carboxy-3-phenylpropyl)amino]-n-butyryl}-2-oxo-imidazolidine-4-carboxylic acid is obtained as colorless crystals. Yield: 87.7% The product is gradually decomposed at about 175° C.

$[\alpha]_D^{25}$ −31.4° (C=1, 1N hydrochloric acid:methanol=1:4)

IR $\nu_{max}^{nujol}$ (cm$^{-1}$): 1735, 1685

(3) 2.3 g of tert.-butyl (4S)-1-benzyl-3-{(2R)-2-[N-((1S)-1-benzyloxycarbonyl-3-phenylpropyl)amino]-n-butyryl}-2-oxo-imidazolidine-4-carboxylate and 40 ml of a 13% hydrogen chloride-dioxane solution are treated in the same manner as described in Example 10-(4), whereby 1.8 g of (4S)-1-benzyl-3-{(2R)-2-[N-((1S)-1-benzyloxycarbonyl-3-phenylpropyl)amino]-n-butyryl}-2-oxo-imidazolidine-4-carboxylic acid hydrochloride are obtained as colorless crystals. Yield: 80.9%

M.p. 177°–178° C. (decomp.)

IR $\nu_{max}^{nujol}$ (cm$^{-1}$): 1730, 1680

(4) 1.65 g of (4S)-1-benzyl-3-{(2R)-2-[N-((1S)-1-benzyloxycarbonyl-3-phenylpropyl)amino]-n-butyryl}-2-oxo-imidazolidine-4-carboxylic acid hydrochloride are suspended in ethyl acetate, and the suspension is neutralized with an aqueous sodium bicarbonate solution. The ethyl acetate layer is collected from the mixture, and the aqueous layer is extracted with ethyl acetate. The ethyl acetate layer and said extract are combined, washed with water, and then dried. The ethyl acetate solution is concentrated under reduced pressure to remove solvent. The residue thus obtained is dissolved in 20 ml of methanol, and 50 mg of palladium black are added thereto. The mixture is treated in the same manner as described in Example 10-(5), whereby 1.2 g of (4S)-1-benzyl-3-{(2R)-2-[N-((1S)-1-carboxy-3-phenylpropyl)amino]-n-butyryl}-2-oxo-imidazolidine-4-carboxylic acid are obtained as colorless crystals. Yield: 92.4%

M.p. 140°–145° C. (The product begins to gradually decompose at 103° C.)

$[\alpha]_D^{25}$ +54.7° (C=1, 1N hydrochloric acid:methanol=1:4)

IR $\nu_{max}^{nujol}$ (cm$^{-1}$): 1735, 1685

EXAMPLE 18

(1) 6.0 g of tert.-butyl (4S)-1-methyl-2-oxo-imidazolidine-4-carboxylate, 5.2 g of 2-bromopropionyl chloride, 3.4 g of potassium tert.-butoxide and 80 ml of tetrahydrofuran are treated in the same manner as described in Example 10-(1), whereby 7.3 g of tert.-butyl (4S)-1-methyl-3-(2-bromopropionyl)-2-oxo-imidazolidine-4-carboxylate are obtained as colorless crystals. Yield: 72.7%

IR $\nu_{max}^{nujol}$ (cm$^{-1}$): 1740, 1680

(2) A mixture of 6.2 g of tert.-butyl (4S)-1-methyl-3-(2-bromopropionyl)-2-oxo-imidazolidine-4-carboxylate, 5.0 g of benzyl (2S)-2-amino-4-phenyl-n-butyrate, 2.6 g of anhydrous potassium carbonate and 15 ml of hexamethylphosphoric triamide is treated in the same manner as described in Example 10-(2). The residue is chromatographed on silica gel column (solvent, toluene:ethyl acetate=4:1), whereby tert.-butyl (4S)-1-methyl-3-{(2S)-2-[N-((1S)-1-benzyloxycarbonyl-3-phenylpropyl)amino]propionyl}-2-oxo-imidazolidine-4-carboxylate (α-isomer) and tert.-butyl (4S)-1-methyl-3-{(2R)-2-[N-((1S)-1-benzyloxycarbonyl-3-phenylpropyl)amino]propionyl}-2-oxo-imidazolidine-4-carboxylate (β-isomer) are obtained, respectively.

α-isomer:
colorless viscous oil Yield: 1.3 g (13.4%)
IR $\nu_{max}^{film}$ (cm$^{-1}$): 3320, 1735, 1680
Mass (m/e): 523 (M$^+$)

β-isomer:
colorless crystals Yield: 5.0 g (51.6%)
M.p. 91°–92° C.
IR $\nu_{max}^{nujol}$ (cm$^{-1}$): 3320, 1725, 1675
Mass (m/e): 523 (M$^+$)

(3) 1.2 g of tert.-butyl (4S)-1-methyl-3-{(2S)-2-[N-((1S)-1-benzyloxycarbonyl-3-phenylpropyl)amino]propionyl}-2-oxo-imidazolidine-4-carboxylate and 20 ml of a 13% hydrogen chloride-dioxane solution are treated in the same manner as described in Example 10-(3), whereby 0.9 g of (4S)-1-methyl-3-{(2S)-2-[N-((1S)-1-benzyloxycarbonyl-3-phenylpropyl)amino]propionyl}-2-oxo-imidazolidine-4-carboxylic acid is obtained as colorless viscous oil. This oil (0.9 g) and 50 mg of palladium black are treated in the same manner as described in Example 10-(5), whereby 0.7 g of (4S)-1-methyl-3-{(2S)-2-[N-((1S)-1-carboxy-3-phenylpropyl)amino]propionyl}-2-oxo-imidazolidine-4-carboxylic acid is obtained as colorless crystals. Yield: 80.9% The physico-chemical properties of this product are identical with those of the sample obtained in Example 4-(2).

(4) 4.8 g of tert.-butyl (4S)-1-methyl-3-{(2R)-2-[N-((1S)-1-benzyloxycarbonyl-3-phenylpropyl)amino]propionyl}-2-oxo-imidazolidine-4-carboxylate and 50 ml of a 13% hydrogen chloride-dioxane solution are treated in the same manner as described in Example 10-(4), whereby 4.3 g of (4S)-1-methyl-3-{(2R)-2-[N-((1S)-1-benzyloxycarbonyl-3-phenylpropyl)amino]propionyl}-2-oxo-imidazolidine-4-carboxylic acid hydrochloride are obtained as colorless crystals. Yield: 93.1%

M.p. 198°–199° C. (decomp.)

(5) 2.7 g of (4S)-1-methyl-3-{(2R)-2-[N-((1S)-1-benzyloxycarbonyl-3-phenylpropyl)amino]propionyl}-2-oxo-imidazolidine-4-carboxylic acid hydrochloride and 100 mg of palladium black are treated in the same manner as described in Example 10-(6), whereby 1.8 g of (4S)-1-methyl-3-{(2R)-2-[N-((1S)-1-carboxy-3-phenylpropyl)amino]propionyl}-2-oxo-imidazolidine-4-carboxylic acid hydrochloride are obtained as colorless crystals. Yield: 81.2%

M.p. 124°–125° C.

$[\alpha]_D^{25} +9.2°$ (C=0.75, 1N hydrochloric acid:methanol=1:4)

IR $\nu_{max}^{nujol}$ (cm$^{-1}$): 3505, 3350, 1725, 1690

EXAMPLE 19

(1) A mixture of 4.5 g of tert.-butyl (4S)-1-methyl-3-(2-bromopropionyl)-2-oxo-imidazolidine-4-carboxylate, 3.8 g of benzyl (2S)-2-amino-n-decanoate, 2.0 g of anhydrous potassium carbonate and 15 ml of hexamethylphosphoric triamide is treated in the same manner as described in Example 10-(2). The residue is chromatographed on silica gel column (solvent, chloroform:ethyl acetate=20:1), whereby tert.-butyl (4S)-1-methyl-3-{(2S)-2-[N-((1S)-1-benzyloxycarbonyl-n-nonyl)amino]propionyl}-2-oxo-imidazolidine-4-carboxylate (α-isomer) and tert.-butyl (4S)-1-methyl-3-{(2R)-2-[N-((1S)-1-benzyloxycarbonyl-n-nonyl)amino]propionyl}-2-oxo-imidazolidine-4-carboxylate (β-isomer) are obtained, respectively.

α-isomer:
colorless viscous oil Yield: 1.0 g (14.0%)
IR $\nu_{max}^{film}$ (cm$^{-1}$): 3320, 1735, 1680
Mass (m/e): 531 (M+)

β-isomer:
colorless viscous oil Yield: 4.6 g (64.4%)
IR $\nu_{max}^{film}$ (cm$^{-1}$): 3320, 1740, 1680
Mass (m/e): 531 (M+)

(2) 0.8 g of tert.-butyl (4S)-1-methyl-3-{(2S)-2-[N-((1S)-1-benzyloxycarbonyl-n-nonyl)amino]propionyl}-2-oxo-imidazolidine-4-carboxylate and 20 ml of a 13% hydrogen chloride-dioxane solution are treated in the same manner as described in Example 10-(3), whereby 0.65 g of (4S)-1-methyl-3-{(2S)-2-[N-((1S)-1-benzyloxycarbonyl-n-nonyl)amino]propionyl}-2-oxo-imidazolidine-4-carboxylic acid is obtained as colorless viscous oil. This oil (0.65 g) and 20 mg of palladium black are treated in the same manner as described in Example 10-(5), whereby 0.5 g of (4S)-1-methyl-3-{(2S)-2-[N-((1S)-1-carboxy-n-nonyl)amino]propionyl}-2-oxo-imidazolidine-4-carboxylic acid is obtained as colorless crystals. Yield: 86.2% The physico-chemical properties of this product are identical with those of the sample obtained in Example 5-(2).

(3) 60 ml of a hydrogen chloride-dioxane solution are added to 4.4 g of tert.-butyl (4S)-1-methyl-3-{(2R)-2-[N-((1S)-1-benzyloxycarbonyl-n-nonyl)amino]propionyl}-2-oxo-imidazolidine-4-carboxylate, and the mixture is allowed to stand at room temperature overnight. The mixture is concentrated under reduced pressure to remove solvent. The residue is triturated with ether, whereby 3.5 g of (4S)-1-methyl-3-{(2R)-2-[N-((1S)-1-benzyloxycarbonyl-n-nonyl)amino]propionyl}-2-oxo-imidazolidine-4-carboxylic acid hydrochloride are obtained as colorless crystals. Yield: 88.9%

M.p. 169°–170° C.

(4) 2.4 g of (4S)-1-methyl-3-{(2R)-2-[N-((1S)-1-benzyloxycarbonyl-n-nonyl)amino]propionyl}-2-oxo-imidazolidine-4-carboxylic acid hydrochloride and 100 mg of palladium black are treated in the same manner as described in Example 10-(6), whereby 1.5 g of (4S)-1-methyl-3-{(2R)-2-[N-((1S)-1-carboxy-n-nonyl)amino]propionyl}-2-oxo-imidazolidine-4-carboxylic acid hydrochloride are obtained as colorless powder. Yield: 70.5%

M.p. 135°–136° C.

$[\alpha]_D^{25} -6.6°$ (C=1, 1N hydrochloric acid:methanol=1:4)

IR $\nu_{max}^{nujol}$ (cm$^{-1}$): 3550, 1730, 1685

EXAMPLE 20

(1) 750 mg of (2S)-2-[N-((1S)-1-n-butoxycarbonyl-3-phenylpropyl)amino]propionic acid, 280 mg of 1-hydroxysuccinimide, 530 mg of dicyclohexylcarbodiimide and 575 mg of benzyl (4S)-1-methyl-2-oxo-imidazolidine-4-carboxylate are treated in the same manner as described in Example 1-(1). The residue is purified by silica gel chromatography (solvent, toluene:ethyl acetate=4:1), whereby 704 mg of benzyl (4S)-1-methyl-3-{(2S)-2-[N-((1S)-1-n-butoxycarbonyl-3-phenylpropyl)amino]propionyl}-2-oxo-imidazolidine-4-carboxylate are obtained as colorless viscous oil. Yield: 55%

IR $\nu_{max}^{film}$ (cm$^{-1}$): 3320, 1730, 1680
Mass (m/e): 523 (M+)

(2) 670 mg of benzyl (4S)-1-methyl-3-{(2S)-[N-((1S)-1-n-butoxycarbonyl-3-phenylpropyl)amino]propionyl}-2-oxo-imidazolidine-4-carboxylate, 20 ml of methanol and 20 mg of palladium black are treated in the same manner as described in Example 1-(2). The residue is crystallized with n-hexane, whereby 480 mg of (4S)-1-methyl-3-{(2S)-2-[N-((1S)-1-n-butoxycarbonyl-3-phenylpropyl)amino]propionyl}-2-oxo-imidazolidine-4-carboxylic acid are obtained as colorless crystals. Yield: 86.5%

M.p. 77°–79° C.

$[\alpha]_D^{23} -67.9°$ (C=0.5, ethanol)
IR $\nu_{max}^{nujol}$ (cm$^{-1}$): 3300, 1730, 1690, 1610
Mass (m/e): 433 (M+)

EXAMPLE 21

(1) 520 mg of (2S)-2-[N-((1S)-1-benzyloxycarbonyl-3-phenylpropyl)amino]propionic acid, 176 mg of 1- hydroxysuccinimide, 316 mg of dicyclohexylcarbodiimide and 420 mg of benzyl (4S)-1-n-butyl-2-oxo-imidazolidine-4-carboxylate are treated in the same manner as described in Example 1-(1). The residue is purified by silica gel chromatography (solvent, chloroform:ethyl acetate=20:1), whereby 350 mg of benzyl (4S)-1-n-butyl-3-{(2S)-2-[N-((1S)-1-benzyloxycarbonyl-3-phenylpropyl)amino]propionyl}-2-oxo-imidazolidine-4-carboxylate are obtained as colorless viscous oil. Yield: 38.4%

IR $\nu_{max}^{film}$ (cm$^{-1}$): 3320, 1725, 1680

Mass (m/e): 599 (M+)

(2) 200 mg of benzyl (4S)-1-n-butyl-3-{(2S)-2-[N-((1S)-1-benzyloxycarbonyl-3-phenylpropyl)amino]propionyl}-2-oxo-imidazolidine-4-carboxylate, 10 ml of methanol and 10 mg of palladium black are treated in the same manner as described in Example 1-(2). The residue is crystallized with ether, whereby 125 mg of (4S)-1-n-butyl-3-{(2S)-2-[N-((1S)-1-carboxy-3-phenylpropyl)amino]propionyl}-2-oxo-imidazolidine-4-carboxylic acid are obtained as colorless crystals. Yield: 89%

M.p. 192°–195° C. (decomp.)

$[\alpha]_D^{24}$ −74.7° (C=1, aqueous 5% sodium bicarbonate solution)

IR $\nu_{max}^{nujol}$ (cm$^{-1}$): 1740, 1690

PREPARATION OF STARTING COMPOUNDS

Preparation 1

(1) 5.1 g of (4S)-3-benzyloxycarbonyl-2-oxo-imidazolidine-4-carboxylic acid (Liebich's Annalen der Chemie 529 (1937), page 1) are dissolved in 20 ml of pyridine, and 50 ml of tert.-butanol are added thereto. The solution is cooled to a temperature below −5° C., and 3.5 g of phosphorous oxychloride are added dropwise thereto. The mixture is stirred at the same temperature for about 30 minutes and then at room temperature for 3 hours. The reaction mixture is poured into 200 ml of ice-water, and extracted with ethyl acetate. The extract is washed with 1% hydrochloric acid, an aqueous sodium bicarbonate solution and water, successively. Then, the extract is dried and evaporated to remove solvent. The residue obtained is crystallized with a mixture of ether and n-hexane. 5.5 g of tert.-butyl (4S)-3-benzyloxycarbonyl-2-oxo-imidazolidine-4-carboxylate are obtained as colorless crystals. Yield: 89.0%

M.p. 138°–139° C.

IR $\nu_{max}^{nujol}$ (cm$^{-1}$): 3270, 1790, 1760, 1740

(2) 9.6 g of tert.-butyl (4S)-3-benzyloxycarbonyl-2-oxo-imidazolidine-4-carboxylate are dissolved in 200 ml of dimethylformamide, and 14.0 g of silver oxide are added thereto. 42.6 g of methyl iodide are added to the mixture at room temperature under stirring, and the mixture is further stirred for 2 days in the dark. The reaction mixture is filtered to remove insoluble materials, and the filtrate is concentrated under reduced pressure. The residue obtained is dissolved in ethyl acetate. Then, the ethyl acetate solution is washed with water, dried and concentrated under reduced pressure. The residue thus obtained is washed with n-hexane. 8.45 g of tert.-butyl (4S)-1-methyl-3-benzyloxycarbonyl-2-oxo-imidazolidine-4-carboxylate are thereby obtained as colorless crystals. Yield: 84.3%

M.p. 102°–103° C.

IR $\nu_{max}^{nujol}$ (cm$^{-1}$): 1790, 1775, 1735

(3) 8.5 g of tert.-butyl (4S)-1-methyl-3-benzyloxycarbonyl-2-oxo-imidazolidine-4-carboxylate are dissolved in 200 ml of methanol, and 0.1 g of palladium black is added thereto. The mixture is shaken at room temperature in hydrogen gas atmosphere under atmospheric pressure. After the reaction the catalyst is removed by filtration, and the filtrate is concentrated under reduced pressure. The residue obtained is washed with n-hexane. 5.0 g of tert.-butyl (4S)-1-methyl-2-oxo-imidazolidine-4-carboxylate are obtained as colorless crystals. Yield: 98.2%

M.p. 135°–136° C.

IR $\nu_{max}^{nujol}$ (cm$^{-1}$): 3300, 1735, 1700

Preparation 2

9.6 g of tert.-butyl (4S)-3-benzyloxycarbonyl-2-oxo-imidazolidine-4-carboxylate are dissolved in 200 ml of acetone, and 8.3 g of anhydrous potassium carbonate and 14.2 g of methyl iodide are added thereto. The mixture is stirred at room temperature for 6 days. The reaction mixture is treated in the same manner as described in Preparation 1-(2), whereby 9.0 g of tert.-butyl (4S)-1-methyl-3-benzyloxycarbonyl-2-oxo-imidazolidine-4-carboxylate are obtained as colorless crystals. Yield: 89.8% The physico-chemical properties of this product are identical with those of the sample obtained in Preparation 1-(2).

Preparation 3

(1) A mixture of 9.6 g of tert.-butyl (4S)-3-benzyloxycarbonyl-2-oxo-imidazolidine-4-carboxylate, 8.3 g of potassium carbonate, 20 g of benzyl bromide and 200 ml of acetone is stirred at room temperature for 3 days. Then, the reaction mixture is treated in the same manner as described in Preparation 1-(2). 9.3 g of tert.-butyl (4S)-1-benzyl-3-benzyloxycarbonyl-2-oxo-imidazolidine-4-carboxylate are obtained as colorless viscous oil. Yield: 75.6%

IR $\nu_{max}^{film}$ (cm$^{-1}$): 1790, 1740, 1715

(2) 7.4 g of tert.-butyl (4S)-1-benzyl-3-benzyloxycarbonyl-2-oxo-imidazolidine-4-carboxylate, 0.1 g of palladium black and 200 ml of methanol are treated in the same manner as described in Preparation 1-(3). 4.7 g of tert.-butyl (4S)-1-benzyl-2-oxo-imidazolidine-4-carboxylate are obtained as colorless crystals. Yield: 94.3%

M.p. 96°–98° C.

IR $\nu_{max}^{KBr}$ (cm$^{-1}$): 3250, 1730, 1705

Recrystallization of this product from n-hexane gives colorless crystals melting at 105° to 108° C.

$[\alpha]_D^{18}$ +41.4° (C=1, methanol)

Preparation 4

(1) A mixture of 40 g of (4S)-3-benzyloxycarbonyl-2-oxoimidazolidine-4-carboxylic acid, 40 g of benzylalcohol, 6 g of p-toluenesulfonic acid monohydrate and 400 ml of benzene is refluxed for 16 hours under heating. After cooling, the mixture is washed with an aqueous sodium bicarbonate solution, dried and then concentrated under reduced pressure to remove solvent. The residue is triturated with n-hexane, whereby 45.7 g of benzyl (4S)-3-benzyloxycarbonyl-2-oxo-imidazolidine-4-carboxylate are obtained as colorless crystals. Yield: 85.2%

M.p. 109°–110° C.

(2) 30 g of benzyl (4S)-3-benzyloxycarbonyl-2-oxo-imidazolidine-4-carboxylate, 35.2 g of anhydrous potassium carbonate, 72.4 g of benzyl bromide and 240 ml of acetone are vigorously stirred at room temperature for 4 days. The mixture is concentrated under reduced pressure to remove solvent. Ethyl acetate and water are added to the residue, and the ethyl acetate layer is collected therefrom. The ethyl acetate solution is washed with water, dried and then concentrated under reduced pressure to remove solvent. The residue is crystallized with n-hexane and recrystallized from a mixture of ethyl acetate and n-hexane, whereby 34.0 g of benzyl (4S)-1-benzyl-3-benzyloxycarbonyl-2-oxo-imidazolidine-4-carboxylate are obtained as colorless crystals. Yield: 90.4%

M.p. 102°–103° C.

(3) 26.8 g of benzyl (4S)-1-benzyl-3-benzyloxycarbonyl-2-oxo-imidazolidine-4-carboxylate are dissolved in 120 ml of a 25% hydrogen bromide-acetic acid solution, and the solution is stirred at room temperature for 20 minutes. The reaction solution is concentrated under reduced pressure to remove solvent. Ethyl acetate is added to the residue, and the mixture is neutralized with an aqueous sodium bicarbonate solution. The ethyl acetate layer is collected therefrom, washed with water, dried and then concentrated under reduced pressure to remove solvent. The residue obtained is recrystallized from a mixture of ethyl acetate and isopropyl ether, whereby 15.2 g of benzyl (4S)-1-benzyl-2-oxo-imidazolidine-4-carboxylate are obtained as colorless flakes. Yield: 81.1%

M.p. 116°–117° C.
IR $\nu_{max}^{nujol}$ (cm$^{-1}$): 3420, 1720, 1700, 1660
Mass (m/e): 310 (M+)

Preparation 5

(1) A mixture of 25 g of benzyl (4S)-3-benzyloxycarbonyl-2-oxo-imidazolidine-4-carboxylate, 29.3 g of anhydrous potassium carbonate, 50 g of methyl iodide and 200 ml of acetone is vigorously stirred at room temperature for 5 days. The mixture is concentrated under reduced pressure to remove solvent. Ethyl acetate and water are added to the residue, and the ethyl acetate layer is collected therefrom. The ethyl acetate solution is dried and concentrated under reduced pressure. The residue obtained is purified by silica gel chromatography and then triturated with ether. 18.2 g of benzyl (4S)-1-methyl-3-benzyloxycarbonyl-2-oxo-imidazolidine-4-carboxylate are thereby obtained as colorless crystals. Yield: 60.7%

M.p. 120°–122° C.

(2) 10 g of benzyl (4S)-1-methyl-3-benzyloxycarbonyl-2-oxo-imidazolidine-4-carboxylate and 40 ml of a hydrogen bromide-acetic acid solution are treated in the same manner as described in Preparation 4-(3), whereby 5.3 g of benzyl (4S)-1-methyl-2-oxo-imidazolidine-4-carboxylate are obtained as colorless crystals. Yield: 83.3%

M.p. 94°–95° C.
IR $\nu_{max}^{nujol}$ (cm$^{-1}$): 3250, 1745, 1710, 1670
Mass (m/e): 234 (M+)

Preparation 6

(1) A mixture of 21.7 g of L-alanine benzyl ester, 33.0 g of ethyl 2-bromo-4-phenyl-n-butyrate, 20.2 g of anhydrous potassium carbonate and 60 ml of hexamethylphosphoric triamide is stirred at room temperature for 3 days. Ether is added to the reaction mixture, and the ether layer is collected therefrom. The ether solution is washed with water, dried and then concentrated to remove solvent. The residue is chromatographed on silica gel column (solvent, toluene:ethyl acetate=10:1). The fractions containing the objective compound are collected and concentrated under reduced pressure. The residue and 11.0 g of maleic acid are dissolved in ethyl acetate, and isopropyl ether is added thereto. The crystalline precipitates are collected by filtration, whereby 21.2 g of benzyl (2S)-2-[N-((1S)-1-ethoxycarbonyl-3-phenylpropyl)amino]propionate maleate are obtained. Yield: 36.1%

(2) An aqueous potassium carbonate solution is added to 21.2 g of benzyl (2S)-2-[N-((1S)-1-ethoxycarbonyl-3-phenylpropyl)amino]propionate maleate, and the mixture is extracted with ether. The extract is washed with an aqueous sodium chloride solution, dried and concentrated under reduced pressure to remove solvent. The residue is dissolved in 250 ml of ethanol, and 200 mg of palladium black are added thereto. The mixture is shaken at room temperature in hydrogen gas atmosphere for 2 hours under atmospheric pressure. Insoluble materials are filtered off, and the filtrate is concentrated under reduced pressure to remove solvent. The residue is crystallized with ether, whereby 9.86 g of (2S)-2-[N-((1S)-1-ethoxycarbonyl-3-phenylpropyl)amino]propionic acid are obtained as colorless crystals. Yield: 80.8%

M.p. 150°–152° C.
$[\alpha]_D^{17}$ +17.6° (C=1, ethanol)
IR $\nu_{max}^{nujol}$ (cm$^{-1}$): 1745, 1600
Mass (m/e): 279 (M+)

Preparation 7

(1) A mixture of 20.4 g of L-alanine benzyl ester, 32.0 g of ethyl 2-bromo-n-decanoate, 19 g of anhydrous potassium carbonate, 60 ml of hexamethylphosphoric triamide and 10.6 g of maleic acid are treated in the same manner as described in Preparation 6-(1), whereby 16.8 g of benzyl (2S)-2-[N-((1S)-1-ethoxycarbonyl-n-nonyl)amino]propionate maleate are obtained. Yield: 29.9%

(2) 16.8 g of benzyl (2S)-2-[N-((1S)-1-ethoxycarbonyl-n-nonyl)amino]propionate maleate and 200 mg of palladium black are treated in the same manner as described in Preparation 6-(2). The residue is crystallized with a mixture of ether and n-hexane. 7.42 g of (2S)-2-[N-((1S)-1-ethoxycarbonyl-n-nonyl)amino]propionic acid are obtained as colorless crystals. Yield: 75.9%

M.p. 127°–128° C.
$[\alpha]_D^{17}$ +9.6° (C=1, ethanol)
IR $\nu_{max}^{nujol}$ (cm$^{-1}$): 1750, 1620, 1580
Mass (m/e): 287 (M+)

Preparation 8

(1) A mixture of 6.05 g of L-alanine benzyl ester, 10.1 g of n-butyl 2-bromo-4-phenyl-n-butyrate, 4.9 g of potassium carbonate and 20 ml of hexamethylphosphoric triamide is stirred at room temperature for 3 days. 100 ml of ether and 40 ml of water are added to the mixture, and ether layer is collected therefrom. Ether solution is washed with water, dried, and then concentrated to remove solvent. The residue is chromatographed on silica gel column (solvent, toluene:ethyl acetate=13:1), whereby 2.6 g of benzyl (2S)-2[N-((1S)-1-n-butoxycarbonyl-3-phenylpropyl)amino]propionate are obtained as colorless viscous oil. Yield: 19.4%

IR $\nu_{max}^{film}$ (cm$^{-1}$): 3320, 1735
Mass (m/e): 397 (M+)

(2) 2.6 g of benzyl (2S)-[N-((1S)-1-n-butoxycarbonyl-3-phenylpropyl)amino]propionate are dissolved in 40 ml of methanol and 50 mg of palladium black are added thereto. The mixture is shaken at room temperature in hydrogen gas atmosphere under atmospheric pressure.

Insoluble materials are filtered off, and the filtrate is concentrated under reduced pressure to remove solvent. The residue is purified by silica gel chromatography (solvent, chloroform:ethanol=15:1), whereby 1.29 g of (2S)-2-[N-((1S)-1-n-butoxycarbonyl-3-phenylpropyl)amino]propionic acid are obtained as colorless crystals. Yield: 64.2%

M.p. 156°-158° C.
$[\alpha]_D^{23}$ +8.5° (C=0.5, ethanol)
IR $\nu_{max}^{nujol}$ (cm$^{-1}$): 1740, 1600
Mass (m/e): 307 (M$^+$)

Preparation 9

(1) A mixture of 5.5 g of benzyl (4S)-3-benzyloxycarbonyl-2-oxo-imidazolidine-4-carboxylate, 14.3 g of n-butyl iodide, 6.4 g of potassium carbonate and 11 ml of hexamethylphosphoric triamide is stirred at room temperature for 4 days. 150 ml of ether and 100 ml of water are added to the mixture, and ether layer is collected therefrom. Ether solution is dried and concentrated to remove solvent. The residue is purified by silica gel chromatography (solvent, toluene:ethyl acetate=4:1), whereby 1.92 g of benzyl (4S)-1-n-butyl-3-benzyloxycarbonyl-2-oxo-imidazolidine-4-carboxylate are obtained as colorless viscous oil. Yield: 30.1%

IR $\nu_{max}^{film}$ (cm$^{-1}$): 1790, 1740, 1660
Mass (m/e): 410 (M$^+$)

(2) 15 ml of 25% hydrogen bromide-acetic acid solution are added to 1.46 g of benzyl (4S)-1-n-butyl-3-benzyloxycarbonyl-2-oxo-imidazolidine-4-carboxylate, and the mixture is stirred at room temperature for 30 minutes. The mixture is concentrated under reduced pressure to remove solvent. 30 ml of ethyl acetate are added to the residue, and the mixture is neutralized with an aqueous saturated sodium bicarbonate solution. Ethyl acetate layer is collected from the mixture, washed with water, dried, and then concentrated to remove solvent. The residue is purified by silica gel chromatography (solvent, chloroform:ethyl acetate=6:1), whereby 560 mg of benzyl (4S)-1-n-butyl-2-oxo-imidazolidine-4-carboxylate are obtained as colorless crystals. Yield: 57%

M.p. 53°-54° C.
IR $\nu_{max}^{nujol}$ (cm$^{-1}$): 3200, 1745, 1730, 1700
Mass (m/e): 276 (M$^+$)

What we claim is:

1. A compound of the formula:

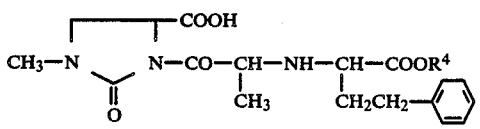

wherein R$^4$ is lower alkyl, or a pharmaceutically acceptable salt thereof.

2. The compound claimed in claim 1 which is 1-methyl-3-{2-[N-(1-ethoxycarbonyl-3-phenylpropyl)amino]-propionyl}-2-oxo-imidazolidine-4-carboxylic acid or a pharmaceutically acceptable salt thereof.

3. The compound claimed in claim 1 which is (4S)-1-methyl-3-{(2S)-2-[N-((1S)-1-ethoxycarbonyl-3-phenylpropyl)amino]propionyl}-2-oxo-imidazolidine-4-carboxylic acid or a pharmaceutically acceptable salt thereof.

4. A hypotensive pharmaceutical composition which comprises a therapeutically effective amount of an active compound of the formula:

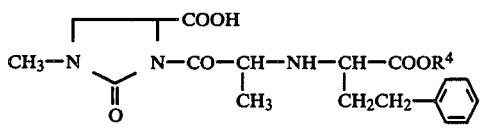

wherein R$^4$ is lower alkyl, or a pharmaceutically acceptable salt thereof and a pharmaceutically acceptable carrier therefor.

5. The hypotensive pharmaceutical composition of claim 4, wherein said active compound is 1-methyl-3-{2-[N-(1-ethoxycarbonyl-3-phenylpropyl)amino]-propionyl}-2-oxo-imidazolidine-4-carboxylic acid or a pharmaceutically acceptable salt thereof.

6. The hypotensive pharmaceutical compositon of claim 4, wherein said active compound is (4S)-1-methyl-3-{2-[N-((1S)-1-ethoxycarbonyl-3-phenylpropyl)amino]propiopyl}-2-oxo-imidazolidine-4-carboxylic acid or a pharmaceutically acceptable salt thereof.

7. A method of producing a hypotensive effect on a warm-blooded animal comprising administering to said warm-blooded animal an effective amount of a compound of the formula:

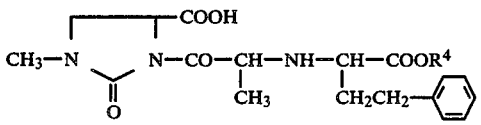

wherein R$^4$ is lower alkyl, or a pharmaceutically acceptable salt thereof.

8. The method of producing a hypotensive effect on a warm-blooded animal, in accordance with claim 7, wherein said compound is 1-methyl-3-{2-[N-(1-ethoxycarbonyl-3-phenylpropyl)amino]propionyl}-2-oxo-imidazolidine-4-carboxylic acid or a pharmaceutically acceptable salt thereof.

9. The method of producing a hypotensive effect on a warm-blooded animal, in accordance with claim 7, wherein said compound is (4s)-1-methyl-3-{(2S)-2-[N-((1S)-1-ethoxycarbonyl-3-phenylpropyl)amino]propionyl}-2-oxo-imidazolidine-4-carboxylic acid or a pharmaceutically acceptable salt thereof.

* * * * *